United States Patent [19]

Dinsmore et al.

[11] Patent Number: 5,780,492
[45] Date of Patent: Jul. 14, 1998

[54] INHIBITORS OF FARNESYL-PROTEIN TRANSFERASE

[75] Inventors: Christopher J. Dinsmore, North Wales; Theresa M. Williams, Harleysville, both of Pa.

[73] Assignee: Merck & Co., Inc., Rahway, N.J.

[21] Appl. No.: 826,317

[22] Filed: Mar. 27, 1997

Related U.S. Application Data

[60] Provisional application No. 60/014,777 Apr. 3, 1996.

[51] Int. Cl.$^6$ .................. A61K 31/415; C07D 403/06; C07D 403/08; C07D 403/10; C07D 403/02; C07D 233/61

[52] U.S. Cl. .............. 514/397; 514/402; 548/314.4; 548/314.7; 548/336.1; 548/346.1; 548/324.5; 546/343

[58] Field of Search .................. 548/314.4; 514/397, 514/402

[56] References Cited

U.S. PATENT DOCUMENTS

| | | | |
|---|---|---|---|
| 5,451,592 | 9/1995 | Reitz et al. | 514/340 |
| 5,576,313 | 11/1996 | Fisher et al. | 514/211 |

FOREIGN PATENT DOCUMENTS

| | | |
|---|---|---|
| 0 064 705 A1 | 11/1982 | European Pat. Off. |
| 0 508 393 A1 | 10/1992 | European Pat. Off. |
| WO94/08990 | 4/1994 | WIPO |
| WO94/11347 | 5/1994 | WIPO |
| WO96/30343 | 10/1996 | WIPO |
| WO 96/37204 | 11/1996 | WIPO |

OTHER PUBLICATIONS

Exp. Opin. Ther. Patents, vol. 5(12), pp. 1269–1271 (1995), by S. L. Graham.
Exp. Opin. Ther. Patents, vol. 6(12) (1996), pp. 1295–1304, by S. L. Graham, et al.
J. of Biol. Chem., vol. 268, No. 11, pp. 7617–7620 (1993), by J. B. Gibbs, et al.
J. of Biol. Chem., vol. 269, No. 44, pp. 27706–27714 (1994), by G. L. James, et al. I.
J. of Biol. Chem., vol. 270, No. 11, pp. 6221–6226 (1995), by G. L. James, et al. II.
Science, vol. 260, pp. 1934–1937 (1993), by N. E. Kohl, et al. I.
Proc. Natl. Acad. Sci. USA, vol. 91, pp. 9141–9145 (1994), by N. E. Kohl, et al. II.
Nature Medicine, vol. 1, No. 8, pp. 792–797 (1995), by N. E. Kohl, et al. III.
Cancer Research, vol. 55, pp. 5302–5309 (1995), by L. Sepp-Lorenzino, et al.

*Primary Examiner*—Floyd D. Higel
*Attorney, Agent, or Firm*—David A. Muthard; Mark R. Daniel; Dianne Pecoraro

[57] ABSTRACT

The present invention is directed to compounds which inhibit farnesyl-protein transferase (FTase) and the farnesylation of the oncogene protein Ras. The invention is further directed to chemotherapeutic compositions containing the compounds of this invention and methods for inhibiting farnesyl-protein transferase and the farnesylation of the oncogene protein Ras.

26 Claims, No Drawings

INHIBITORS OF FARNESYL-PROTEIN TRANSFERASE

DOMESTIC PRIORITY CLAIM

The priority of U.S. Provisional Application No. 60/014,777, filed on Apr. 3, 1996, now abandoned, is claimed.

BACKGROUND OF THE INVENTION

The Ras proteins (Ha-Ras, Ki4a-Ras, Ki4b-Ras and N-Ras) are part of a signalling pathway that links cell surface growth factor receptors to nuclear signals initiating cellular proliferation. Biological and biochemical studies of Ras action indicate that Ras functions like a G-regulatory protein. In the inactive state, Ras is bound to GDP. Upon growth factor receptor activation Ras is induced to exchange GDP for GTP and undergoes a conformational change. The GTP-bound form of Ras propagates the growth stimulatory signal until the signal is terminated by the intrinsic GTPase activity of Ras, which returns the protein to its inactive GDP bound form (D. R. Lowy and D. M. Willumsen, Ann. Rev. Biochem. 62:851–891 (1993)). Mutated ras genes (Ha-ras, Ki4a-ras, Ki4b-ras and N-ras) are found in many human cancers, including colorectal carcinoma, exocrine pancreatic carcinoma, and myeloid leukemias. The protein products of these genes are defective in their GTPase activity and constitutively transmit a growth stimulatory signal.

Ras must be localized to the plasma membrane for both normal and oncogenic functions. At least 3 post-translational modifications are involved with Ras membrane localization, and all 3 modifications occur at the C-terminus of Ras. The Ras C-terminus contains a sequence motif termed a "CAAX" or "Cys-Aaa$^1$-Aaa$^2$-Xaa" box (Cys is cysteine, Aaa is an aliphatic amino acid, the Xaa is any amino acid) (Willumsen et al., Nature 310:583–586 (1984)). Depending on the specific sequence, this motif serves as a signal sequence for the enzymes farnesyl-protein transferase or geranylgeranyl-protein transferase, which catalyze the alkylation of the cysteine residue of the CAAX motif with a $C_{15}$ or $C_{20}$ isoprenoid, respectively. (S. Clarke., Ann. Rev. Biochem. 61:355–386 (1992); W. R. Schafer and J. Rine, Ann. Rev. Genetics 30:209–237 (1992)). The Ras protein is one of several proteins that are known to undergo post-translational farnesylation. Other farnesylated proteins include the Ras-related GTP-binding proteins such as Rho, fungal mating factors, the nuclear lamins, and the gamma subunit of transducin. James, et al., J. Biol. Chem. 269, 14182 (1994) have identified a peroxisome associated protein Pxf which is also farnesylated. James, et al., have also suggested that there are farnesylated proteins of unknown structure and function in addition to those listed above.

Inhibition of farnesyl-protein transferase has been shown to block the growth of Ras-transformed cells in soft agar and to modify other aspects of their transformed phenotype. It has also been demonstrated that certain inhibitors of farnesyl-protein transferase selectively block the processing of the Ras oncoprotein intracellularly (N. E. Kohl et al., Science, 260:1934–1937 (1993) and G. L. James et al., Science, 260:1937–1942 (1993). Recently, it has been shown that an inhibitor of farnesyl-protein transferase blocks the growth of ras-dependent tumors in nude mice (N. E. Kohl et al., Proc. Natl. Acad. Sci U.S.A., 91:9141–9145 (1994) and induces regression of mammary and salivary carcinomas in ras transgenic mice (N. E. Kohl et al., Nature Medicine, 1:792–797 (1995).

Indirect inhibition of farnesyl-protein transferase in vivo has been demonstrated with lovastatin (Merck & Co., Rahway, N.J.) and compactin (Hancock et al., ibid; Casey et al., ibid; Schafer et al., Science 245:379 (1989)). These drugs inhibit HMG-CoA reductase, the rate limiting enzyme for the production of polyisoprenoids including farnesyl pyrophosphate. Farnesyl-protein transferase utilizes farnesyl pyrophosphate to covalently modify the Cys thiol group of the Ras CAAX box with a farnesyl group (Reiss et al., Cell, 62:81–88 (1990); Schaber et al., J. Biol. Chem., 265:14701–14704 (1990); Schafer et al., Science, 249:1133–1139 (1990); Manne et al., Proc. Natl. Acad. Sci U.S.A., 87:7541–7545 (1990)). Inhibition of farnesyl pyrophosphate biosynthesis by inhibiting HMG-CoA reductase blocks Ras membrane localization in cultured cells. However, direct inhibition of farnesyl-protein transferase would be more specific and attended by fewer side effects than would occur with the required dose of a general inhibitor of isoprene biosynthesis.

Inhibitors of farnesyl-protein transferase (FPTase) have been described in two general classes. The first are analogs of farnesyl diphosphate (FPP), while the second class of inhibitors is related to the protein substrates (e.g., Ras) for the enzyme. The peptide derived inhibitors that have been described are generally cysteine containing molecules that are related to the CAAX motif that is the signal for protein prenylation. (Schaber et al., ibid; Reiss et. al., ibid; Reiss et al., PNAS, 88:732–736 (1991)). Such inhibitors may inhibit protein prenylation while serving as alternate substrates for the farnesyl-protein transferase enzyme, or may be purely competitive inhibitors (U.S. Pat. No. 5,141,851, University of Texas; N. E. Kohl et al., Science, 260:1934–1937 (1993); Graham, et al., J. Med. Chem., 37, 725 (1994)). In general, deletion of the thiol from a CAAX derivative has been shown to dramatically reduce the inhibitory potency of the compound. However, the thiol group potentially places limitations on the therapeutic application of FPTase inhibitors with respect to pharmacokinetics, pharmacodynamics and toxicity. Therefore, a functional replacement for the thiol is desirable.

It has recently been reported that farnesyl-protein transferase inhibitors are inhibitors of proliferation of vascular smooth muscle cells and are therefore useful in the prevention and thereapy of arteriosclerosis and diabetic disturbance of blood vessels (JP H7-112930).

It has recently been disclosed that certain tricyclic compounds which optionally incorporate a piperidine moiety are inhibitors of FPTase (WO 95/10514, WO 95/10515 and WO 95/10516). Imidazole-containing inhibitors of farnesyl protein transferase have also been disclosed (WO 95/09001 and EP 0 675 112 A1).

It is, therefore, an object of this invention to develop peptidomimetic compounds that do not have a thiol moiety, and that will inhibit farnesyl-protein transferase and thus, the post-translational farnesylation of proteins. It is a further object of this invention to develop chemotherapeutic compositions containing the compounds of this invention and methods for producing the compounds of this invention.

SUMMARY OF THE INVENTION

The present invention comprises small molecule imidazolidinone-containing compounds which inhibit the farnesyl-protein transferase. The instant compounds lack a thiol moiety and thus offer unique advantages in terms of improved pharmacokinetic behavior in animals, prevention of thiol-dependent chemical reactions, such as rapid autoxidation and disulfide formation with endogenous thiols, and reduced systemic toxicity. Further contained in this invention are chemotherapeutic compositions containing these farnesyl transferase inhibitors and methods for their production.

The compounds of this invention are illustrated by the formula I:

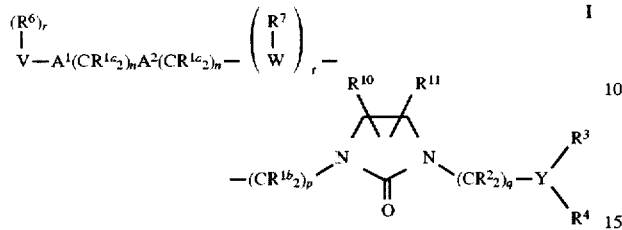

DETAILED DESCRIPTION OF THE INVENTION

The compounds of this invention are useful in the inhibition of farnesyl-protein transferase and the farnesylation of the oncogene protein Ras. In a first embodiment of this invention, the inhibitors of farnesyl-protein transferase are illustrated by the formula I:

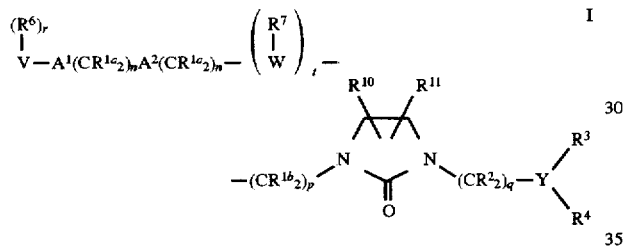

wherein:

$R^{1a}$, $R^{1b}$ and $R^2$ are independently selected from:
a) hydrogen,
b) aryl, heterocycle, $C_3$–$C_{10}$ cycloalkyl, $C_2$–$C_6$ alkenyl, $C_2$–$C_6$ alkynyl, $R^8O$—, $R^9S(O)_m$—, $R^8C(O)NR^8$—, CN, $NO_2$, $(R^8)_2N$—$C(NR^8)$—, $R^8C(O)$—, $R^8OC(O)$—, $N_3$, —$N(R^8)_2$, or $R^9OC(O)NR^8$—,
c) $C_1$–$C_6$ alkyl unsubstituted or substituted by aryl, heterocyclic, $C_3$–$C_{10}$ cycloalkyl, $C_2$–$C_6$ alkenyl, $C_2$–$C_6$ alkynyl, $R^8O$—, $R^9S(O)_m$—, $R^8C(O)NR^8$—, CN, $(R^8)_2N$—$C(NR^8)$—, $R^8C(O)$—, $R^8OC(O)$—, $N_3$, —$N(R^8)_2$, or $R^9OC(O)$—$NR^8$—;

$R^3$ and $R^4$ are independently selected from F, Cl, Br, $N(R^8)_2$, $CF_3$, $NO_2$, $(R^8)O$—, $(R^9)S(O)_m$—, $(R^8)C(O)NH$—, $H_2N$—$C(NH)$—, $(R^8)C(O)$—, $(R^8)OC(O)$—, $N_3$, CN, $CF_3(CH_2)_nO$—, $(R^9)OC(O)NR^8$—, $C_1$–$C_{20}$ alkyl, substituted or unsubstituted aryl and substituted or unsubstituted heterocycle;

$R^6$ is independently selected from:
a) hydrogen,
b) aryl, heterocycle, $C_3$–$C_{10}$ cycloalkyl, $C_2$–$C_6$ alkenyl, $C_2$–$C_6$ alkynyl, perfluoroalkyl, F, Cl, Br, $R^8O$—, $R^9S(O)_m$—, $R^8C(O)NR^8$—, CN, $NO_2$, $R^8_2N$—$C(NR^8)$—, $R^8C(O)$—, $R^8OC(O)$—, $N_3$, —$N(R^8)_2$, or $R^9OC(O)NR^8$—, and
c) $C_1$–$C_6$ alkyl unsubstituted or substituted by aryl, heterocycle, $C_3$–$C_{10}$ cycloalkyl, $C_2$–$C_6$ alkenyl, $C_2$–$C_6$ alkynyl, perfluoroalkyl, F, Cl, Br, $R^8O$—, $R^9S(O)_m$—, $R^8C(O)NH$—, CN, $H_2N$—$C(NH)$—, $R^8C(O)$—, $R^8OC(O)$—, $N_3$, —$N(R^8)_2$, or $R^8OC(O)NH$—;

$R^7$ is attached to a substitutable carbon on W and is selected from:
a) hydrogen,
b) $C_2$–$C_6$ alkenyl, $C_2$–$C_6$ alkynyl, perfluoroalkyl, F, Cl, Br, $R^8O$—, $R^9S(O)_m$—, $R^8C(O)NR^8$—, CN, $NO_2$, $(R^8)_2N$—$C$—$(NR^8)$—, $R^8C(O)$—, $R^8OC(O)$—, $N_3$, —$N(R^8)_2$, or $R^9OC(O)NR^8$—, and
c) $C_1$–$C_6$ alkyl unsubstituted or substituted by perfluoroalkyl, F, Cl, Br, $R^8O$—, $R^9S(O)_m$—, $R^8C(O)NR^8$—, CN, $(R^8)_2N$—$C(NR^8)$—, $R^8C(O)$—, $R^8OC(O)$—, $N_3$, —$N(R^8)_2$, or $R^9OC(O)NR^8$—;

$R^8$ is independently selected from hydrogen, $C_1$–$C_6$ alkyl, benzyl and aryl;

$R^9$ is independently selected from $C_1$–$C_6$ alkyl and aryl;

$R^{10}$ and $R^{11}$ independently selected from: H;

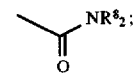

or $C_{1-5}$ alkyl, unbranched or branched, unsubstituted or substituted with one or more of:
1) aryl,
2) heterocycle,
3) $OR^8$,
4) $SR^9$, $SO_2R^9$, or
5)

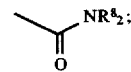

$A^1$ and $A^2$ are independently selected from: a bond, —CH=CH—, —C≡C—, —C(O)—, —C(O)NR$^8$—, —NR$^8$C(O)—, O, —N(R$^8$)—, —S(O)$_2$N(R$^8$)—, —N(R$^8$)S(O)$_2$—, or S(O)$_m$;

V is selected from:
a) hydrogen,
b) heterocycle,
c) aryl,
d) $C_1$–$C_{20}$ alkyl wherein from 0 to 4 carbon atoms are replaced with a a heteroatom selected from O, S, and N, and
e) $C_2$–$C_{20}$ alkenyl, provided that V is not hydrogen if $A^1$ is $S(O)_m$ and V is not hydrogen if $A^1$ is a bond, n is 0 and $A^2$ is $S(O)_m$;

W is a heterocycle;

Y is aryl or heteroaryl;

m is 0, 1 or 2;

n is 0, 1, 2, 3 or 4;

p is 0, 1, 2, 3 or 4;

q is 0, 1, 2, 3 or 4;

r is 0 to 5, provided that r is 0 when V is hydrogen; and t is 0 or 1;

or the pharmaceutically acceptable salts thereof.

A preferred embodiment of the compounds of this invention are illustrated by the formula Ia:

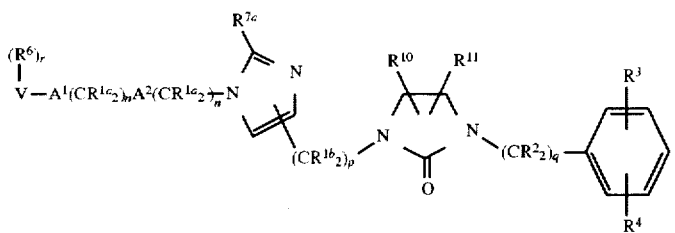

Ia wherein:
$R^{1a}$ and $R^2$ are independently selected from: hydrogen or $C_1$–$C_6$ alkyl;
$R^{1b}$ is independently selected from:
  a) hydrogen,
  b) aryl, heterocycle, cycloalkyl, $R^8O$—, —$N(R^8)_2$ or $C_2$–$C_6$ alkenyl,
  c) $C_1$–$C_6$ alkyl unsubstituted or substituted by aryl, heterocycle, cycloalkyl, alkenyl, $R^8O$—, or —$N(R^8)_2$;
$R^3$ and $R^4$ are independently selected from F, Cl, Br, $N(R^8)_2$, $CF_3$, $NO_2$, $(R^8)O$—, $(R^9)S(O)_m$—, $(R^8)C(O)NH$—, $H_2N$—$C(NH)$—, $(R^8)C(O)$—, $(R^8)OC(O)$—, $N_3$, CN, $(R^9)OC(O)NR^8$—, $C_1$–$C_{20}$ alkyl, substituted or unsubstituted aryl and substituted or unsubstituted heterocycle;
$R^6$ is independently selected from:
  a) hydrogen,
  b) $C_1$–$C_6$ alkyl, $C_2$–$C_6$ alkenyl, $C_2$–$C_6$ alkynyl, $C_1$–$C_6$ perfluoroalkyl, F, Cl, $R^8O$—, $R^8C(O)NR^8$—, CN, $NO_2$, $(R^8)_2N$—$C(NR^8)$—, $R^8C(O)$—, $R^8OC(O)$—, —$N(R^8)_2$, or $R^9OC(O)NR^8$—, and
  c) $C_1$–$C_6$ alkyl substituted by $C_1$–$C_6$ perfluoroalkyl, $R^8O$—, $R^8C(O)NR^8$—, $(R^8)_2N$—$C(NR^8)$—, $R^8C(O)$—, $R^8OC(O)$—, —$N(R^8)_2$, or $R^9OC(O)NR^8$—;
$R^{7a}$ is hydrogen or methyl;

$R^8$ is independently selected from hydrogen, $C_1$–$C_6$ alkyl, benzyl and aryl;
$R^9$ is independently selected from $C_1$–$C_6$ alkyl and aryl;
$R^{10}$ and $R^{11}$ are independently selected from: H;

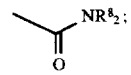

or $C_{1-5}$ alkyl, unbranched or branched, unsubstituted or substituted with one or more of:
  1) aryl,
  2) heterocycle,
  3) $OR^8$,
  4) $SR^9$, $SO_2R^9$, or

5)

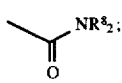

$A^1$ and $A^2$ are independently selected from: a bond, —CH=CH—, —C≡C—, —C(O)—, —C(O)NR^8—, O, —N(R^8)—, or $S(O)_m$;
V is selected from:
  a) hydrogen,
  b) heterocycle selected from pyrrolidinyl, imidazolyl, pyridinyl, thiazolyl, pyridonyl, 2-oxopiperidinyl, indolyl, quinolinyl, isoquinolinyl, and thienyl,
  c) aryl,
  d) $C_1$–$C_{20}$ alkyl wherein from 0 to 4 carbon atoms are replaced with a a heteroatom selected from O, S, and N, and
  e) $C_2$–$C_{20}$ alkenyl, and
provided that V is not hydrogen if $A^1$ is $S(O)_m$ and V is not hydrogen if $A^1$ is a bond, n is 0 and $A^2$ is $S(O)_m$;
m is 0, 1 or 2;
n is 0, 1, 2, 3 or 4;
p is 0, 1, 2, 3 or 4; and
q is 0, 1, 2, 3 or 4; and
r is 0 to 5, provided that r is 0 when V is hydrogen;
or the pharmaceutically acceptable salts thereof.

A second preferred embodiment of the compounds of this invention are illustrated by the formula Ib:

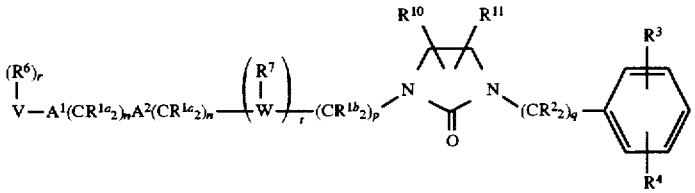

Ib wherein:
$R^{1a}$ and $R^2$ are independently selected from: hydrogen or $C_1$–$C_6$ alkyl;
$R^{1b}$ is independently selected from:
  a) hydrogen,
  b) aryl, heterocycle, cycloalkyl, $R^8O$—, —$N(R^8)_2$ or $C_2$–$C_6$ alkenyl,
  c) $C_1$–$C_6$ alkyl unsubstituted or substituted by aryl, heterocycle, cycloalkyl, alkenyl, $R^8O$—, or —$N(R^8)_2$;
$R^3$ and $R^4$ are independently selected from F, Cl, Br, $N(R^8)_2$, $CF_3$, $NO_2$, $(R^8)O$—, $(R^9)S(O)_m$—, $(R^8)C(O)NH$—, $H_2N$—$C(NH)$—, $(R^8)C(O)$—, $(R^8)OC(O)$—, $N_3$, CN, $(R^9)OC(O)NR^8$—, $C_1$–$C_{20}$ alkyl, substituted or unsubstituted aryl and substituted or unsubstituted heterocycle;
$R^6$ is independently selected from:
  a) hydrogen,
  b) $C_1$–$C_6$ alkyl, $C_2$–$C_6$ alkenyl, $C_2$–$C_6$ alkynyl, $C_1$–$C_6$ perfluoroalkyl, F, Cl, $R^8O$—, $R^8C(O)NR^8$—, CN, $NO_2$, $(R^8)_2N$—$C(NR^8)$—, $R^8C(O)$—, $R^8OC(O)$—, —$N(R^8)_2$, or $R^9OC(O)NR^8$—, and c) $C_1$–$C_6$ alkyl substituted by $C_1$–$C_6$ perfluoroalkyl, $R^8O$—, $R^8C(O)NR^8$—, $(R^8)_2N$—$C(NR^8)$—, $R^8C(O)$—, $R^8OC(O)$—, —$N(R^8)_2$, or $R^9OC(O)NR^8$—;

$R^7$ is selected from: hydrogen and $C_1$–$C_6$ alkyl;

$R^8$ is independently selected from hydrogen, $C_1$–$C_6$ alkyl, benzyl and aryl;

$R^9$ is independently selected from $C_1$–$C_6$ alkyl and aryl;

$R^{10}$ and $R^{11}$ are independently selected from: H;

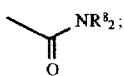

or $C_{1-5}$ alkyl, unbranched or branched, unsubstituted or substituted with one or more of:

1) aryl,
2) heterocycle,
3) $OR^8$,
4) $SR^9$, $SO_2R^9$, or
5)

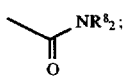

$A^1$ and $A^2$ are independently selected from: a bond, —CH=CH—, —C≡C—, —C(O)—, —C(O)$NR^8$—, O, —$N(R^8)$—, or $S(O)_m$;

V is selected from:

a) hydrogen,
b) heterocycle selected from pyrrolidinyl, imidazolyl, pyridinyl, thiazolyl, pyridonyl, 2-oxopiperidinyl, indolyl, quinolinyl, isoquinolinyl, and thienyl,
c) aryl,
d) $C_1$–$C_{20}$ alkyl wherein from 0 to 4 carbon atoms are replaced with a a heteroatom selected from O, S, and N, and
e) $C_2$–$C_{20}$ alkenyl, and provided that V is not hydrogen if $A^1$ is $S(O)_m$ and V is not hydrogen if $A^1$ is a bond, n is 0 and $A^2$ is $S(O)_m$;

W is a heterocycle selected from pyrrolidinyl, pyridinyl, thiazolyl, pyridonyl, 2-oxopiperidinyl, indolyl, quinolinyl, or isoquinolinyl;

m is 0, 1 or 2;
n is 0, 1, 2, 3 or 4;
p is 0, 1, 2, 3 or 4;
q is 0, 1, 2, 3 or 4;
r is 0 to 5, provided that r is 0 when V is hydrogen; and
t is 1;

or the pharmaceutically acceptable salts thereof.

In a more preferred embodiment of this invention, the inhibitors of farnesyl-protein transferase are illustrated by the formula Ic:

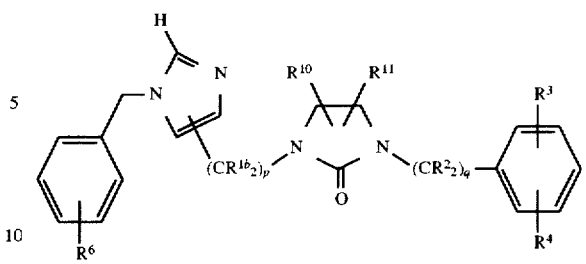

wherein:

$R^{1b}$ is independently selected from:
a) hydrogen,
b) aryl, heterocycle, cycloalkyl, $R^8O$—, —$N(R^8)_2$ or $C_2$–$C_6$ alkenyl,
c) $C_1$–$C_6$ alkyl unsubstituted or substituted by aryl, heterocycle, cycloalkyl, alkenyl, $R^8O$—, or —$N(R^8)_2$;

$R^2$ are independently selected from: hydrogen or $C_1$–$C_6$ alkyl;

$R^3$ and $R^4$ are independently selected from F, Cl, Br, $N(R^8)_2$, $CF_3$, $NO_2$, $(R^8)O$—, $(R^9)S(O)_m$—, $(R^8)C(O)NH$—, $H_2N$—$C(NH)$—, $(R^8)C(O)$—, $(R^8)OC(O)$—, $N_3$, CN, $(R^9)OC(O)NR^8$—, $C_1$–$C_{20}$ alkyl, substituted or unsubstituted aryl and substituted or unsubstituted heterocycle;

$R^6$ is independently selected from:
a) hydrogen,
b) $C_1$–$C_6$ alkyl, $C_2$–$C_6$ alkenyl, $C_2$–$C_6$ alkynyl, $C_1$–$C_6$ perfluoroalkyl, F, Cl, $R^8O$—, $R^8C(O)NR^8$—, CN, $NO_2$, $(R^8)_2N$—$C(NR^8)$—, $R^8C(O)$—, $R^8OC(O)$—, —$N(R^8)_2$, or $R^9OC(O)NR^8$—, and
c) $C_1$–$C_6$ alkyl substituted by $C_1$–$C_6$ perfluoroalkyl, $R^8O$—, $R^8C(O)NR^8$—, $(R^8)_2N$—$C(NR^8)$—, $R^8C(O)$—, $R^8OC(O)$—, —$N(R^8)_2$, or $R^9OC(O)NR^8$—;

$R^8$ is independently selected from hydrogen, $C_1$–$C_6$ alkyl, benzyl and aryl;

$R^9$ is independently selected from $C_1$–$C_6$ alkyl and aryl;

$R^{10}$ and $R^{11}$ are independently selected from: H;

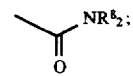

or $C_{1-5}$ alkyl, unbranched or branched, unsubstituted or substituted with one or more of:

1) aryl,
2) heterocycle,
3) $OR^8$,
4) $SR^9$, $SO_2R^9$, or
5)

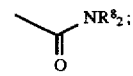

m is 0, 1 or 2;
p is 0, 1, 2, 3 or 4; and
q is 0, 1, 2, 3 or 4;

or the pharmaceutically acceptable salts thereof.

In a second more preferred embodiment of this invention, the inhibitors of farnesyl-protein transferase are illustrated by the formula Id:

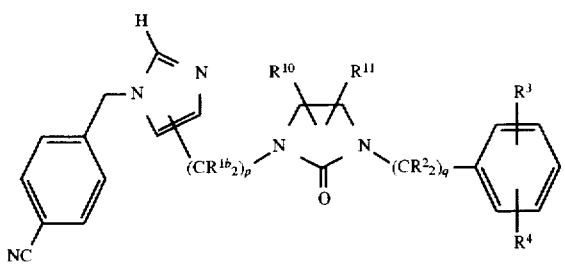

wherein:

$R^{1b}$ is independently selected from:
 a) hydrogen,
 b) aryl, heterocycle, cycloalkyl, $R^8O-$, $-N(R^8)_2$ or $C_2-C_6$ alkenyl,
 c) $C_1-C_6$ alkyl unsubstituted or substituted by aryl, heterocycle, cycloalkyl, alkenyl, $R^8O-$, or $-N(R^8)_2$;

$R^2$ are independently selected from: hydrogen or $C_1-C_6$ alkyl;

$R^3$ and $R^4$ are independently selected from F, Cl, Br, $N(R^8)_2$, $CF_3$, $NO_2$, $(R^8)O-$, $(R^9)S(O)_m-$, $(R^8)C(O)NH-$, $H_2N-C(NH)-$, $(R^8)C(O)-$, $(R^8)OC(O)-$, $N_3$, CN, $(R^9)OC(O)NR^8-$, $C_1-C_{20}$ alkyl, substituted or unsubstituted aryl and substituted or unsubstituted heterocycle;

$R^8$ is independently selected from hydrogen, $C_1-C_6$ alkyl, benzyl and aryl;

$R^9$ is independently selected from $C_1-C_6$ alkyl and aryl;

$R^{10}$ and $R^{11}$ are independently selected from: H;

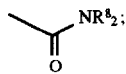

or $C_{1-5}$ alkyl, unbranched or branched, unsubstituted or substituted with one or more of:
 1) aryl,
 2) heterocycle,
 3) $OR^8$,
 4) $SR^9$, $SO_2R^9$, or
 5)

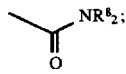

m is 0, 1 or 2;
p is 0, 1, 2, 3 or 4; and
q is 0, 1, 2, 3 or 4;

or the pharmaceutically acceptable salts thereof.

The preferred compounds of this invention are as follows:
(±)-4-(2-Butynyl)-1-(3-chlorophenyl)-3-[1-(4-cyanobenzyl)-5-imidazolylmethyl]-2-imidazolidinone
(S)-4-n-butyl-3-|1-(4-cyanobenzyl)-5-imidazolylmethyl]-1-(2,3-dimethylphenyl)-2-imidazolidinone
1-(3-Chlorophenyl)-3-|1-(4-cyanobenzyl)-5-imidazolylmethyl|-2-imidazolidinone
4-(S)-4-n-Butyl-3-|4-chloro-1-(4-cyanobenzyl)-5-imidazolylmethyl|-1-(2-chloro-5 ,6-dimethylphenyl)-2-imidazolidinone
(S)-1-(3-Chlorobenzyl)-3-[1-(4-cyanobenzyl)-5-imidazolylmethyl]-4-[(2-methanesulfonyl)ethyl]-2-imidazolidinone or the pharmaceutically acceptable salts or optical isomers thereof.

Specific examples of the compounds of the invention are:
(S)-1-(3-Chlorobenzyl)-3-[1-(4-cyanobenzyl)-5-imidazolylmethyl]-4-[(2-methanesulfonyl)ethyl]-2-imidazolidinone

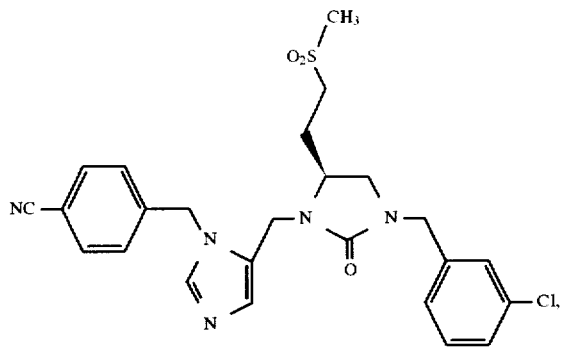

or the pharmaceutically acceptable salts thereof.

The compounds of the present invention may have asymmetric centers and occur as racemates, racemic mixtures, and as individual diastereomers, with all possible isomers, including optical isomers, being included in the present invention. When any variable (e.g. aryl, heterocycle, $R^{1a}$, $R^2$ etc.) occurs more than one time in any constituent, its definition on each occurence is independent at every other occurence. Also, combinations of substituents/or variables are permissible only if such combinations result in stable compounds.

As used herein, "alkyl" is intended to include both branched and straight-chain saturated aliphatic hydrocarbon groups having the specified number of carbon atoms; "alkoxy" represents an alkyl group of indicated number of carbon atoms attached through an oxygen bridge. "Halogen" or "halo" as used herein means fluoro, chloro, bromo and iodo.

As used herein, "aryl" is intended to mean any stable monocyclic or bicyclic carbon ring of up to 7 members in each ring, wherein at least one ring is aromatic. Examples of such aryl elements include phenyl, naphthyl, tetrahydronaphthyl, indanyl, biphenyl, phenanthryl, anthryl or acenaphthyl.

The term heterocycle or heterocyclic, as used herein, represents a stable 5- to 7-membered monocyclic or stable 8- to 11-membered bicyclic heterocyclic ring which is either saturated or unsaturated, and which consists of carbon atoms and from one to four heteroatoms selected from the group consisting of N, O, and S, and including any bicyclic group in which any of the above-defined heterocyclic rings is fused to a benzene ring. The heterocyclic ring may be attached at any heteroatom or carbon atom which results in the creation of a stable structure. Examples of such heterocyclic elements include, but are not limited to, azepinyl, benzimidazolyl, benzisoxazolyl, benzofurazanyl, benzopyranyl, benzothiopyranyl, benzofuryl, benzothiazolyl, benzothienyl, benzoxazolyl, chromanyl, cinnolinyl, dihydrobenzofuryl, dihydrobenzothienyl, dihydrobenzothiopyranyl, dihydrobenzothiopyranyl sulfone, furyl, imidazolidinyl, imidazolinyl, imidazolyl, indolinyl, indolyl, isochromanyl, isoindolinyl, isoquinolinyl, isothiazolidinyl, isothiazolyl, isothiazolidinyl, morpholinyl, naphthyridinyl, oxadiazolyl, 2-oxoazepinyl, 2-oxopiperazinyl, 2-oxopiperdinyl, 2-oxopyrrolidinyl, piperidyl, piperazinyl, pyridyl, pyrazinyl, pyrazolidinyl, pyrazolyl, pyridazinyl, pyrimidinyl, pyrrolidinyl, pyrrolyl, quinazolinyl, quinolinyl, quinoxalinyl, tetrahydrofuryl, tetrahydroisoquinolinyl, tetrahydroquinolinyl, thiamorpholinyl, thiamorpholinyl sulfoxide, thiazolyl, thiazolinyl, thienofuryl, thienothienyl, and thienyl.

As used herein, "heteroaryl" is intended to mean any stable monocyclic or bicyclic carbon ring of up to 7 members in each ring, wherein at least one ring is aromatic and wherein from one to four carbon atoms are replaced by heteroatoms selected from the group consisting of N, O, and S. Examples of such heterocyclic elements include, but are not limited to, benzimidazolyl, benzisoxazolyl, benzofurazanyl, benzopyranyl, benzothiopyranyl, benzofuryl, benzothiazolyl, benzothienyl, benzoxazolyl, chromanyl, cinnolinyl, dihydrobenzofuryl, dihydrobenzothienyl, dihydrobenzothiopyranyl, dihydrobenzothiopyranyl sulfone, furyl, imidazolyl, indolinyl, indolyl, isochromanyl, isoindolinyl, isoquinolinyl, isothiazolyl, naphthyridinyl, oxadiazolyl, pyridyl, pyrazinyl, pyrazolyl, pyridazinyl, pyrimidinyl, pyrrolyl, quinazolinyl, quinolinyl, quinoxalinyl, tetrahydroisoquinolinyl, tetrahydroquinolinyl, thiazolyl, thienofuryl, thienothienyl, and thienyl.

As used herein, the terms "substituted aryl", "substituted heterocycle" and "substituted cycloalkyl" are intended to include the cyclic group which is substituted with 1 or 2 substitutents selected from the group which includes but is not limited to F, Cl, Br, $CF_3$, $NH_2$, $N(C_1-C_6$ alkyl$)_2$, $NO_2$, CN, ($C_1-C_6$ alkyl)O—, —OH, ($C_1-C_6$ alkyl)S(O)$_m$—, ($C_1-C_6$ alkyl)C(O)NH—, $H_2N$—C(NH)—, ($C_1-C_6$ alkyl)C (O)—, ($C_1-C_6$ alkyl)OC(O)—, $N_3$,($C_1-C_6$ alkyl)OC(O) NH— and $C_1-C_{20}$ alkyl.

The term "nitrogen protecting group", as used herein, is as described in U.S. Pat. No. 5,424,328 and includes those groups usually employed in the chemistry of peptides, typically a triphenylmethyl, t-butyloxycarbonyl, acetyl, formyl, di(p-methoxyphenyl)methyl and (p-methoxyphenyl)diphenylmethyl.

Lines drawn into the ring systems from substituents (such as from $R^3$, $R^4$, $R^{10}$, $R^{11}$ etc.) indicate that the indicated bond may be attached to any of the substitutable ring carbon atoms.

Preferably, $R^{1a}$, $R^{1b}$ and $R^2$ are independently selected from: hydrogen, —N($R^8$)$_2$, $R^8$C(O)N$R^8$— or $C_1-C_6$ alkyl unsubstituted or substituted by —N($R^8$)$_2$, $R^8$O— or $R^8$C(O) N$R^8$—.

Preferably, $R^3$ and $R^4$ are independently selected from: hydrogen, perfluoroalkyl, F, Cl, Br, $R^8$O—, $R^9$S(O)$_m$—, CN, $NO_2$, $R^8{}_2$N—C(N$R^8$)—, $R^8$C(O)—, $R^8$OC(O)—, $N_3$, —N($R^8$)$_2$, or $R^9$OC(O)N$R^8$— and $C_1-C_6$ alkyl.

Preferably, $R^6$ is selected from: hydrogen, perfluoroalkyl, F, Cl, Br, $R^8$O—, $R^9$S(O)$_m$—, CN, $NO_2$, $R^8{}_2$N—C(N$R^8$)—, $R^8$C(O)—, $R^8$OC(O)—, $N_3$, —N($R^8$)$_2$, or $R^9$OC(O)N$R^8$— and $C_1-C_6$ alkyl.

Preferably, $R^7$ is hydrogen.

Preferably, $R^8$ is selected from H, $C_1-C_6$ alkyl and benzyl.

Preferably, $R^9$ is selected from $C_1-C_6$ alkyl.

Preferably, $R^{10}$ and $R^{11}$ is selected from H, $C_1-C_6$ alkyl and benzyl.

Preferably, $A^1$ and $A^2$ are independently selected from: a bond, —C(O)N$R^8$—, —N$R^8$C(O)—, O, —N($R^8$)—, —S(O)$_2$N($R^8$)— and —N($R^8$)S(O)$_2$—.

Preferably, V is selected from hydrogen, heterocycle and aryl. Most preferably, V is phenyl.

Preferably, Y is selected from phenyl, furyl, thienyl and pyridyl. Most preferably, Y is phenyl.

Preferably, n, p and r are independently 0, 1, or 2.

Preferably t is 1.

Preferably, when W is imidazolyl, then the substituent $(R^6)_r$—V—$A^1(CR^{1a}{}_2)_nA^2(CR^{1a}{}_2)_n$— is not H, $C_1-C_6$ alkyl or a nitrogen protecting group;

The pharmaceutically acceptable salts of the compounds of this invention include the conventional non-toxic salts of the compounds of this invention as formed, e.g., from non-toxic inorganic or organic acids. For example, such conventional non-toxic salts include those derived from inorganic acids such as hydrochloric, hydrobromic, sulfuric, sulfamic, phosphoric, nitric and the like; and the salts prepared from organic acids such as acetic, propionic, succinic, glycolic, stearic, lactic, malic, tartaric, citric, ascorbic, pamoic, maleic, hydroxymaleic, phenylacetic, glutamic, benzoic, salicylic, sulfanilic, 2-acetoxy-benzoic, fumaric, toluenesulfonic, methanesulfonic, ethane disulfonic, oxalic, isethionic, trifluoroacetic and the like.

It is intended that the definition of any substituent or variable (e.g., $R^{1a}$, $R^8$, n, etc.) at a particular location in a molecule be independent of its definitions elsewhere in that molecule. Thus, —N($R^8$)$_2$ represents —NHH, —NHCH$_3$, —NHC$_2$H$_5$, etc. It is understood that substituents and substitution patterns on the compounds of the instant invention can be selected by one of ordinary skill in the art to provide compounds that are chemically stable and that can be readily synthesized by techniques known in the art, as well as those methods set forth below, from readily available starting materials.

The pharmaceutically acceptable salts of the compounds of this invention can be synthesized from the compounds of this invention which contain a basic moiety by conventional chemical methods. Generally, the salts are prepared either by ion exchange chromatography or by reacting the free base with stoichiometric amounts or with an excess of the desired salt-forming inorganic or organic acid in a suitable solvent or various combinations of solvents.

Reactions used to generate the compounds of this invention are prepared by employing reactions as shown in Schemes 1–13, in addition to other standard manipulations such as ester hydrolysis, cleavage of protecting groups, etc., as may be known in the literature or exemplified in the experimental procedures. Substituents R' and R'CH$_2$—, as shown in the Schemes, represent the substituents $R^8$, $R^9$ and others, depending on the compound of the instant invention that is being synthesized. The variable p' represents p–1.

These reactions may be employed in a linear sequence to provide the compounds of the invention or they may be used to synthesize fragments which are subsequently joined by the alkylation reactions described in the Schemes.

Synopsis of Schemes 1–13

The requisite intermediates are in some cases commercially available, or can be prepared according to literature procedures, for the most part. Schemes 1–4 illustrates the synthesis of one of the preferred embodiments of the instant invention, wherein the variable W is present as a imidazolyl moiety that is substituted with a suitably substituted benzyl group. Substituted protected imidazole alkanols II can be prepared by methods known in the art, such as those described by F. Schneider, Z. Physiol. Chem., 3:206–210 (1961) and C. P. Stewart, Biochem. Journal, 17:130–133 (1923). Benzylation and deprotection of the imidazole alkanol provides intermediate III which can be oxidized to the corresponding aldehyde IV.

The aldehyde whose synthesis is illustrated in Scheme 1 may be reacted with a suitably substituted diamine, which is prepared from the aniline VII and a suitably substituted amino acid V via the protected aldehyde VI as shown in Scheme 2. This coupling with aldehyde IV provides the intermediate compound VIII. The imidazolidinone ring can then be formed by reacting intermediate VIII with triphosgene under standard conditions, such as those illustrated, to provide the instant compound IX.

Scheme 3 illustrates the synthesis of an aldehyde VIa which corresponds to aldehyde VI but which has an unsaturated $R^{10}/R^{11}$ moiety. Subsequent reactions provide the instant compound XII.

A general synthetic route for preparing compounds of the instant invention wherein both $R^{10}$ and $R^{11}$ are hydrogen is illustrated in Scheme 4.

Schemes 5–8 illustrate syntheses of suitably substituted aldehydes useful in the syntheses of the instant compounds wherein the variable W is present as a pyridyl moiety. Similar synthetic strategies for preparing alkanols that incorporate other heterocyclic moieties for variable W are also well known in the art.

The suitably substituted diamine XIII can be reacted with a variety of other aldehydes, such as XIV, as shown in Scheme 9. The product XV is first reacted with triphosgene to form the imidazolidinone ring and then deprotected to give the instant compound XVI. The compound XVI is isolated in the salt form, for example, as a trifluoroacetate, hydrochloride or acetate salt, among others. As shown in Scheme 10. Compound XVI can further be selectively protected to obtain XVII which can subsequently be reductively alkylated with a second aldehyde, such as XVIII, to obtain intermediate XIX. Removal of the protecting group, and conversion to cyclized products such as the dihydroimidazole XX can be accomplished by literature procedures, such as those shown.

If the diamine XIII is reductively alkylated with an aldehyde which also has a protected hydroxyl group, such as XXI in Scheme 11, the product XXII can be reacted with triphosgene to form the imidazolidinone ring and the protecting groups can be subsequently removed to unmask the hydroxyl group (Schemes 11, 12). The alcohol can be oxidized under standard conditions to e.g. an aldehyde, which can then be reacted with a variety of organometallic reagents such as Grignard reagents, to obtain secondary alcohols such as XXIV. In addition, the fully deprotected amino alcohol XXV can be reductively alkylated (under conditions described previously) with a variety of aldehydes to obtain secondary amines, such as XXVI (Scheme 12), or tertiary amines.

The Boc protected amino alcohol XXIII can also be utilized to synthesize 2-aziridinylmethylamides such as XXVII (Scheme 13). Treating XXIII with 1,1'-sulfonyldiimidazole and sodium hydride in a solvent such as dimethylformamide leads to the formation of aziridine XXVII. The aziridine may be reacted with a nucleophile, such as a thiol, in the presence of base to yield, after deprotection, the ring-opened product XXVIII.

In addition, the diamine XIII can be reacted with aldehydes derived from amino acids such as O-alkylated tyrosines, according to standard procedures, to obtain compounds such as XXXII, as shown in Scheme 14. Intermediate XXXII is first reacted with triphosgene to form the imidazolidinone ring before it is further elaborated. When R' is an aryl group, XXXIII can first be hydrogenated to unmask the phenol, and the amine group deprotected with acid to produce XXXIV. Alternatively, the amine protecting group in XXXIII can be removed, and O-alkylated phenolic amines such as XXXV produced.

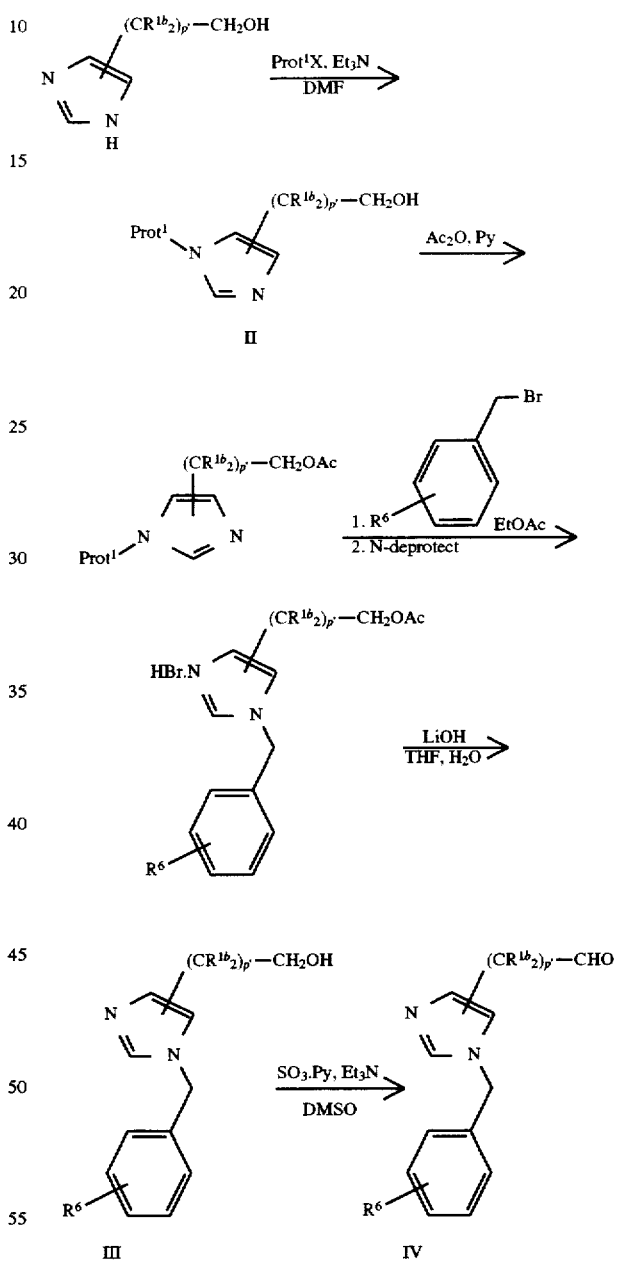

SCHEME 2
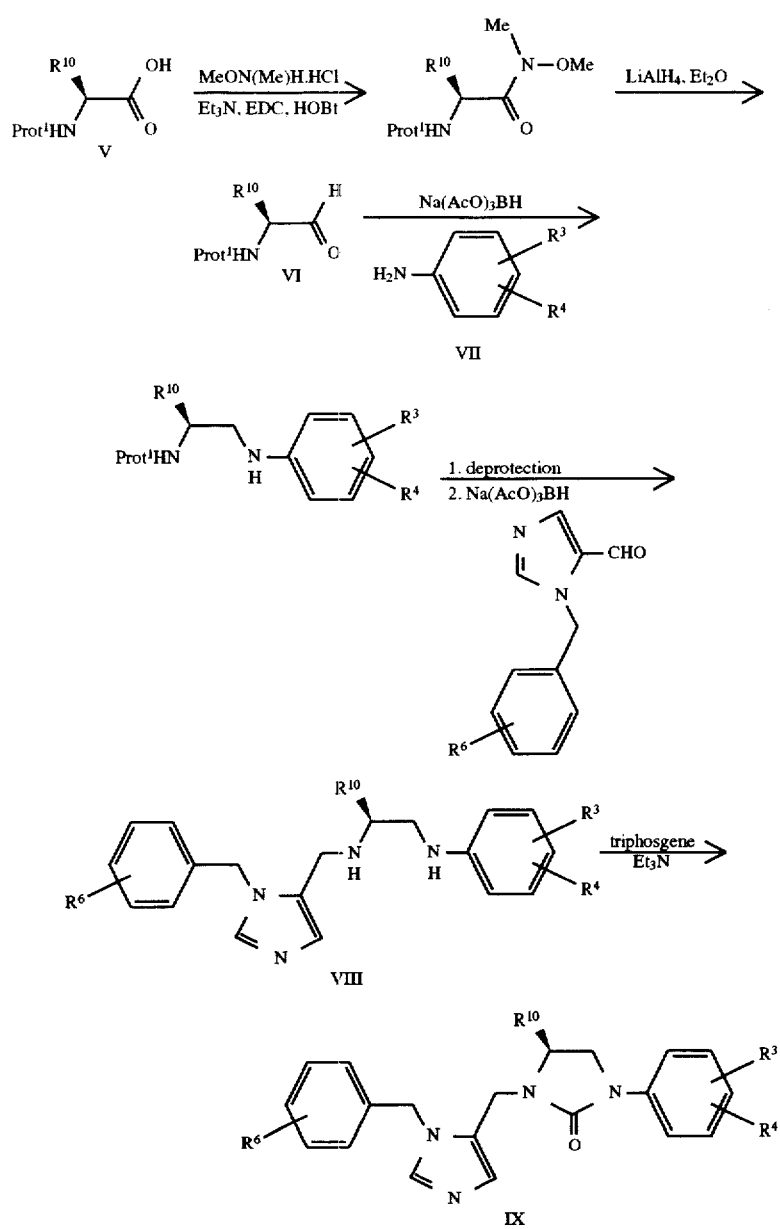
SCHEME 3
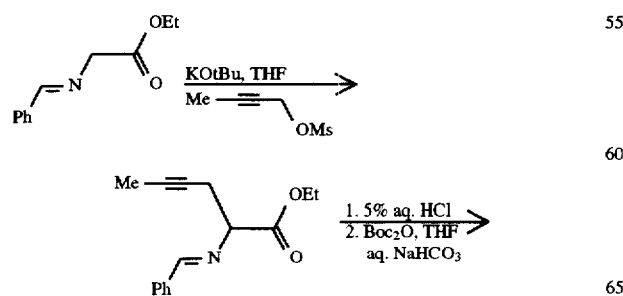
-continued
SCHEME 3
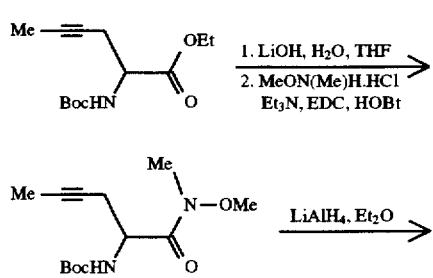

17
-continued
SCHEME 3
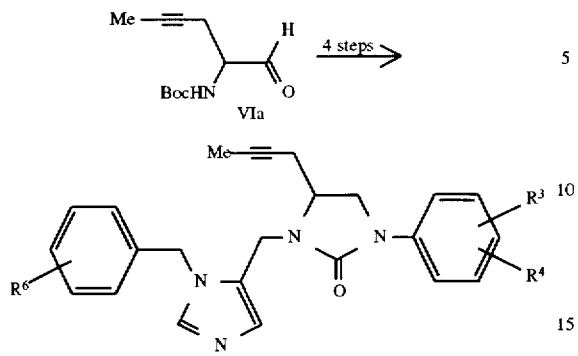
18
-continued
SCHEME 5
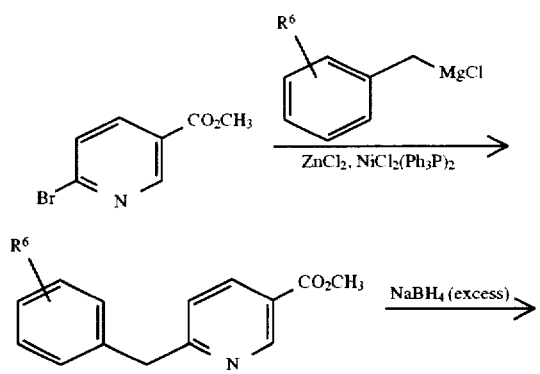
SCHEME 4
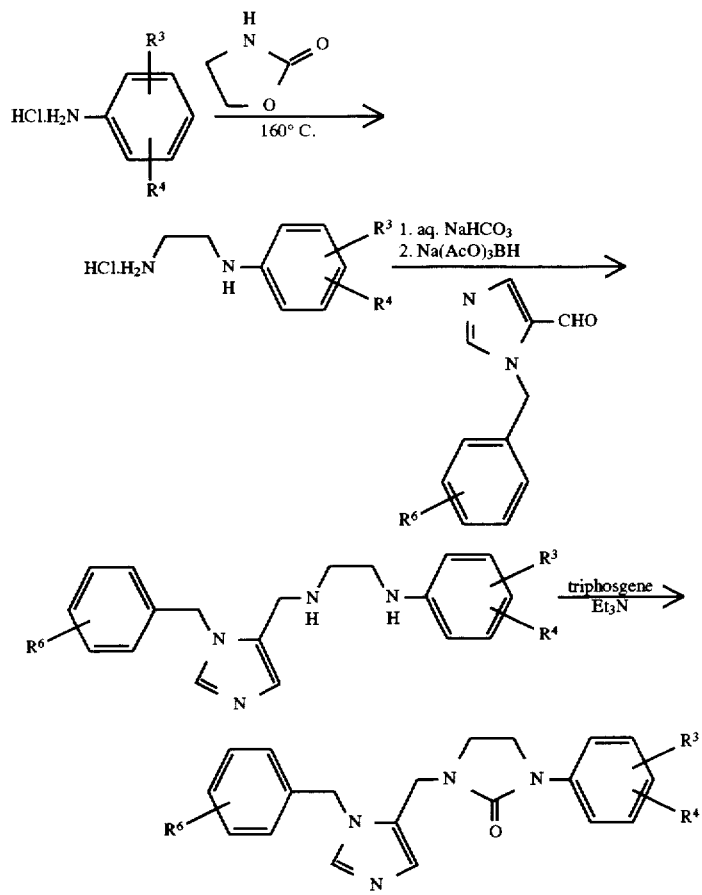
SCHEME 5
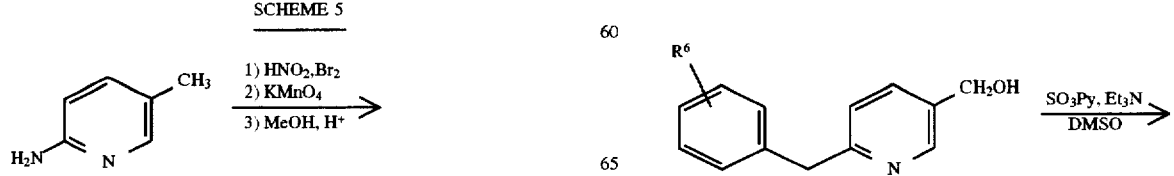

SCHEME 5
-continued
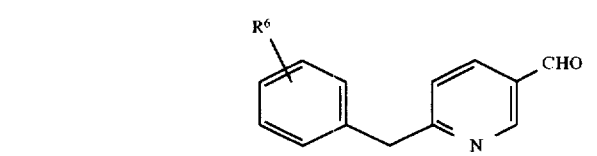
SCHEME 6
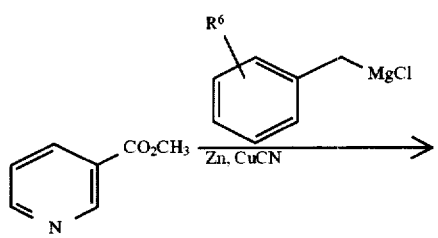
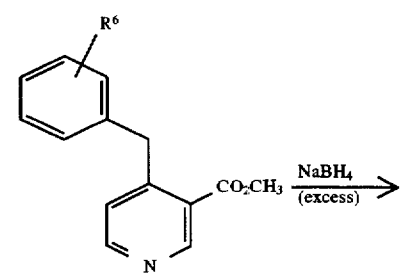
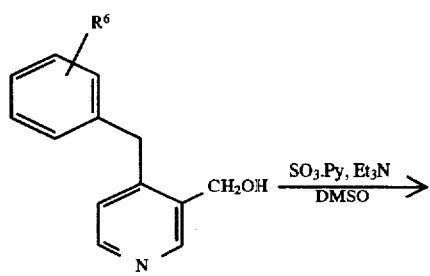
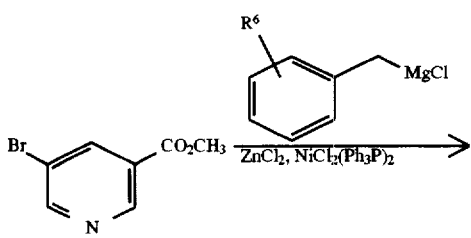
SCHEME 6
-continued
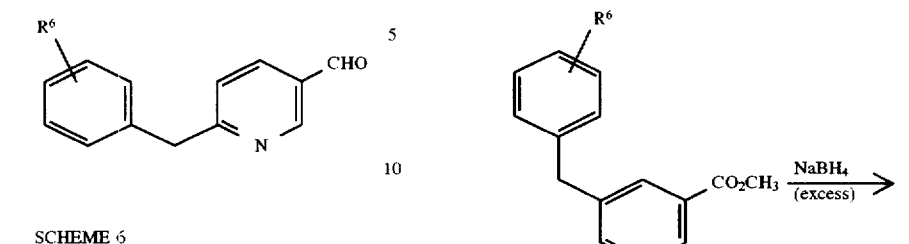
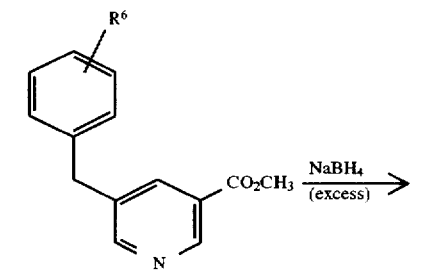
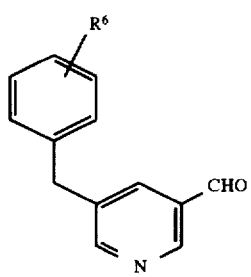
SCHEME 7
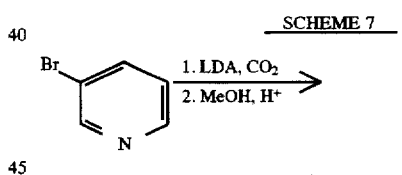
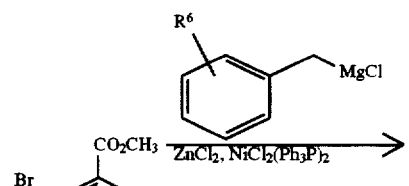
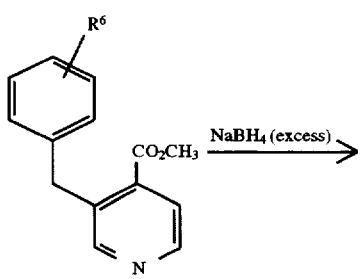

SCHEME 7 -continued
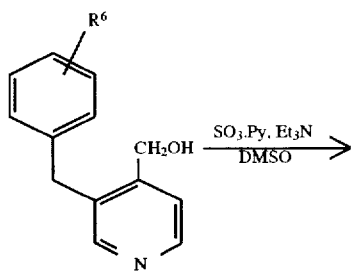
SCHEME 8
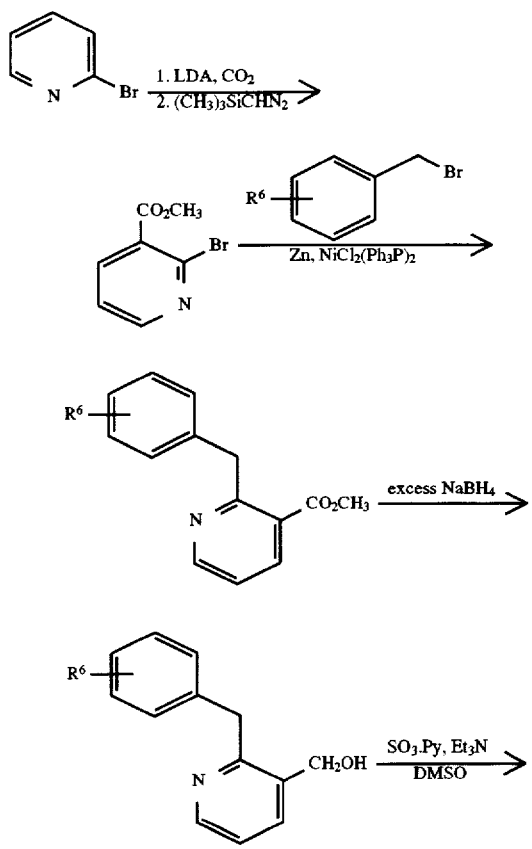
SCHEME 8 -continued
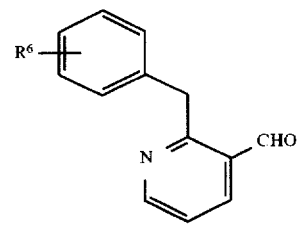
SCHEME 9
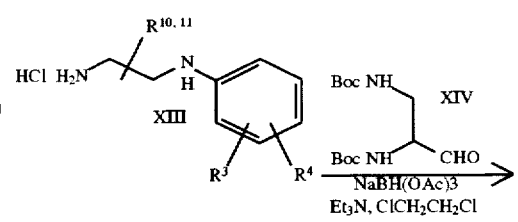
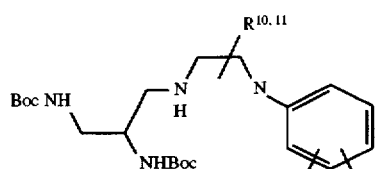
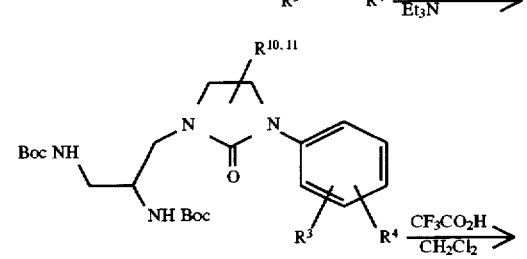
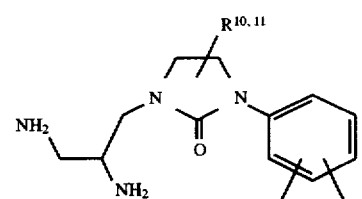
SCHEME 10
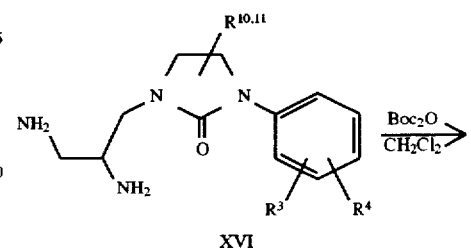

SCHEME 10 -continued
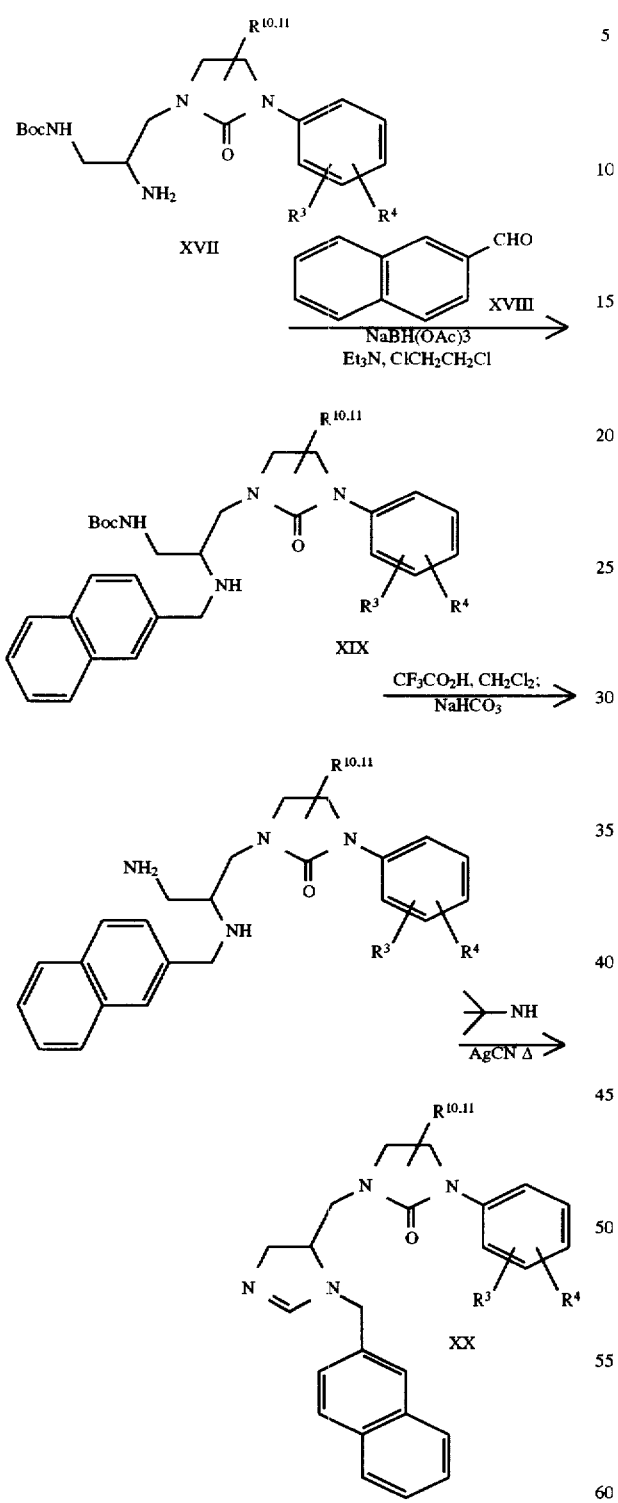
SCHEME 11
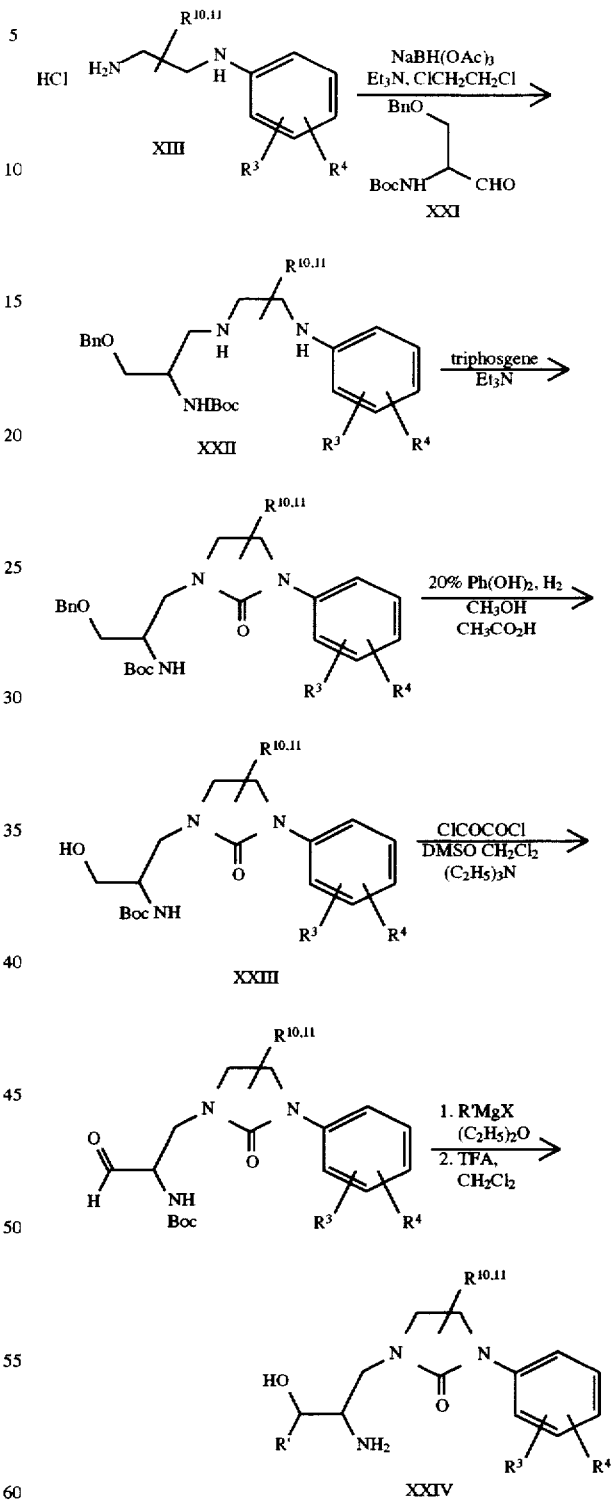

SCHEME 12
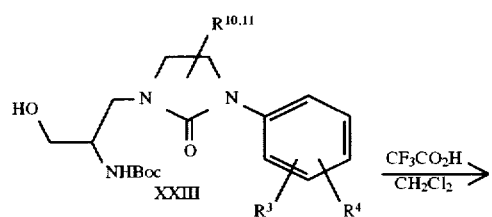
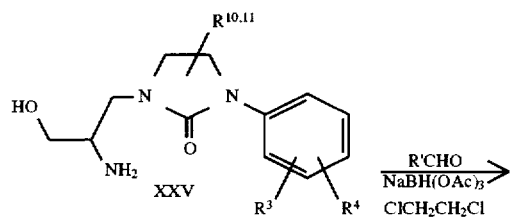
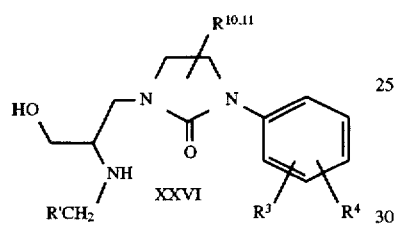
SCHEME 13
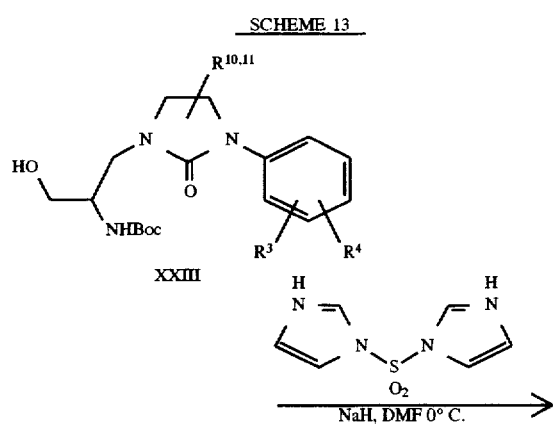
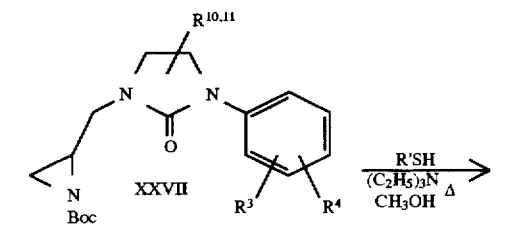
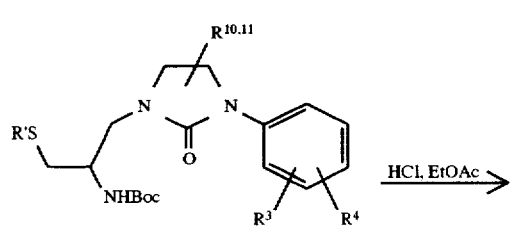
-continued
SCHEME 13
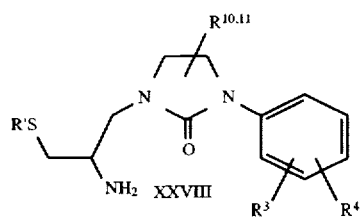
SCHEME 14
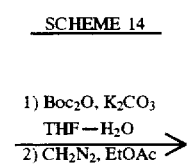
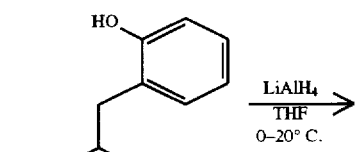
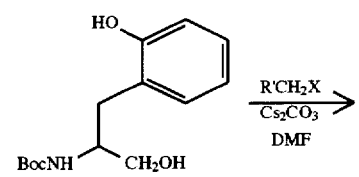
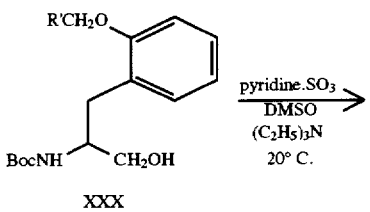
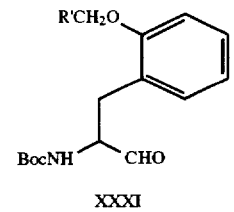
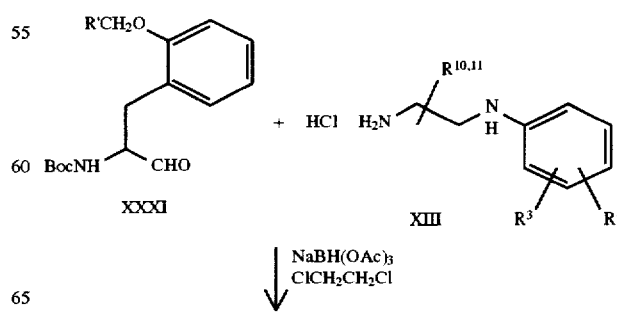

-continued
SCHEME 14

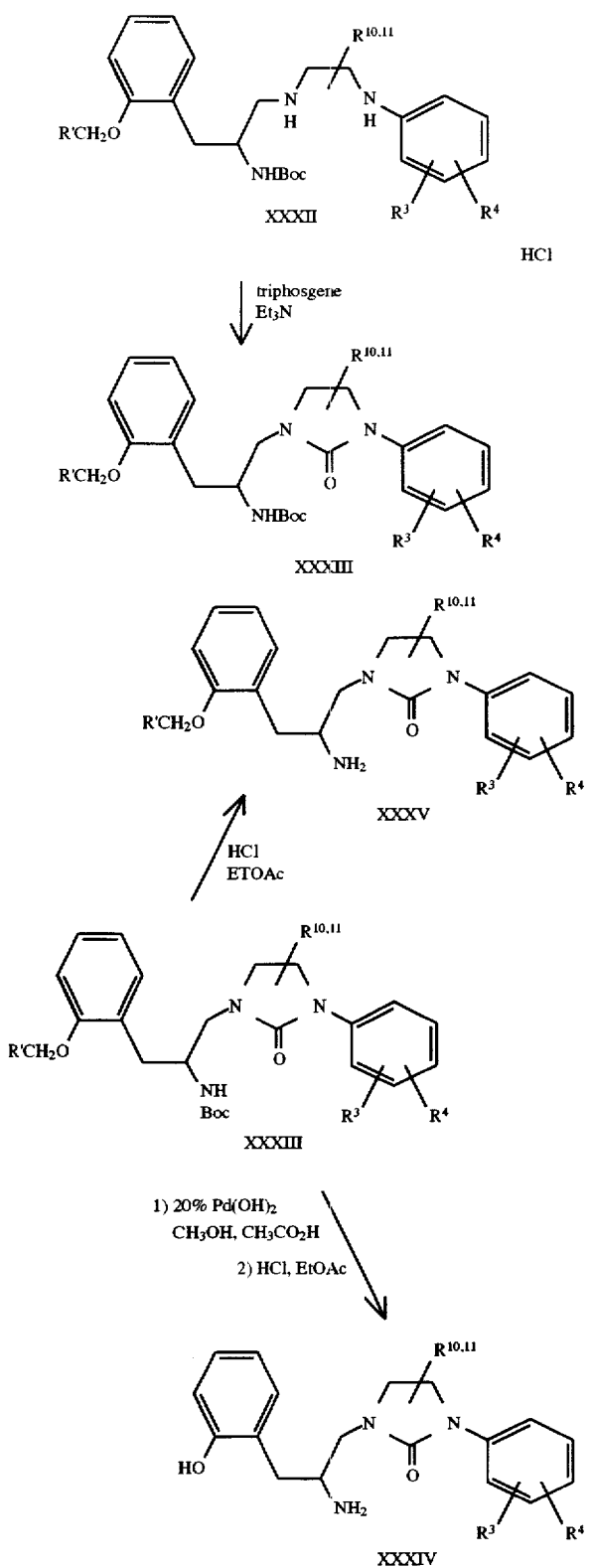

The instant compounds are useful as pharmaceutical agents for mammals, especially for humans. These compounds may be administered to patients for use in the treatment of cancer. Examples of the type of cancer which may be treated with the compounds of this invention include, but are not limited to, colorectal carcinoma, exocrine pancreatic carcinoma, myeloid leukemias and neurological tumors. Such tumors may arise by mutations in the ras genes themselves, mutations in the proteins that can regulate Ras formation (i.e., neurofibromen (NF-1), neu, scr, abl, lck, fyn) or by other mechanisms.

The compounds of the instant invention inhibit farnesyl-protein transferase and the farnesylation of the oncogene protein Ras. The instant compounds may also inhibit tumor angiogenisis, thereby affecting the growth of tumors (J. Rak et al. *Cancer Research*, 55:4575–4580 (1995)). Such anti-angiogenisis properties of the instant compounds may also be useful in the treatment of certain forms of blindness related to retinal vascularization.

The compounds of this invention are also useful for inhibiting other proliferative diseases, both benign and malignant, wherein Ras proteins are aberrantly activated as a result of oncogenic mutation in other genes (i.e., the Ras gene itself is not activated by mutation to an oncogenic form) with said inhibition being accomplished by the administration of an effective amount of the compounds of the invention to a mammal in need of such treatment. For example, a component of NF-1 is a benign proliferative disorder.

The instant compounds may also be useful in the treatment of certain viral infections, in particular in the treatment of hepatitis delta and related viruses (J. S. Glenn et al. *Science*, 256:1331–1333 (1992)).

The compounds of the instant invention are also useful in the prevention of restenosis after percutaneous transluminal coronary angioplasty by inhibiting neointimal formation (C. Indolfi et al. *Nature medicine*, 1:541–545(1995)).

The instant compounds may also be useful in the treatment and prevention of polycystic kidney disease (D. L. Schaffner et al. *American Journal of Pathology*, 142:1051–1060 (1993) and B. Cowley, Jr. et al.*FASEB Journal*, 2:A3160 (1988)).

The compounds of this invention may be administered to mammals, preferably humans, either alone or, preferably, in combination with pharmaceutically acceptable carriers or diluents, optionally with known adjuvants, such as alum, in a pharmaceutical composition, according to standard pharmaceutical practice. The compounds can be administered orally or parenterally, including the intravenous, intramuscular, intraperitoneal, subcutaneous, rectal and topical routes of administration.

For oral use of a chemotherapeutic compound according to this invention, the selected compound may be administered, for example, in the form of tablets or capsules, or as an aqueous solution or suspension. In the case of tablets for oral use, carriers which are commonly used include lactose and corn starch, and lubricating agents, such as magnesium stearate, are commonly added. For oral administration in capsule form, useful diluents include lactose and dried corn starch. When aqueous suspensions are required for oral use, the active ingredient is combined with emulsifying and suspending agents. If desired, certain sweetening and/or flavoring agents may be added. For intramuscular, intraperitoneal, subcutaneous and intravenous use, sterile solutions of the active ingredient are usually prepared, and the pH of the solutions should be suitably adjusted and buffered. For intravenous use, the total concentration of solutes should be controlled in order to render the preparation isotonic.

The present invention also encompasses a pharmaceutical composition useful in the treatment of cancer, comprising the administration of a therapeutically effective amount of the compounds of this invention, with or without pharmaceutically acceptable carriers or diluents. Suitable compositions of this invention include aqueous solutions comprising compounds of this invention and pharmacologically acceptable carriers, e.g., saline, at a pH level, e.g., 7.4. The solutions may be introduced into a patient's intramuscular blood-stream by local bolus injection.

When a compound according to this invention is administered into a human subject, the daily dosage will normally be determined by the prescribing physician with the dosage generally varying according to the age, weight, and response of the individual patient, as well as the severity of the patient's symptoms.

In one exemplary application, a suitable amount of compound is administered to a mammal undergoing treatment for cancer. Administration occurs in an amount between about 0.1 mg/kg of body weight to about 60 mg/kg of body weight per day, preferably of between 0.5 mg/kg of body weight to about 40 mg/kg of body weight per day.

The compounds of the instant invention are also useful as a component in an assay to rapidly determine the presence and quantity of farnesyl-protein transferase (FPTase) in a composition. Thus the composition to be tested may be divided and the two portions contacted with mixtures which comprise a known substrate of FPTase (for example a tetrapeptide having a cysteine at the amine terminus) and farnesyl pyrophosphate and, in one of the mixtures, a compound of the instant invention. After the assay mixtures are incubated for an sufficient period of time, well known in the art, to allow the FPTase to farnesylate the substrate, the chemical content of the assay mixtures may be determined by well known immunological, radiochemical or chromatographic techniques. Because the compounds of the instant invention are selective inhibitors of FPTase, absence or quantitative reduction of the amount of substrate in the assay mixture without the compound of the instant invention relative to the presence of the unchanged substrate in the assay containing the instant compound is indicative of the presence of FPTase in the composition to be tested.

It would be readily apparent to one of ordinary skill in the art that such an assay as described above would be useful in identifying tissue samples which contain farnesyl-protein transferase and quantitating the enzyme. Thus, potent inhibitor compounds of the instant invention may be used in an active site titration assay to determine the quantity of enzyme in the sample. A series of samples composed of aliquots of a tissue extract containing an unknown amount of farnesyl-protein transferase, an excess amount of a known substrate of FPTase (for example a tetrapeptide having a cysteine at the amine terminus) and famesyl pyrophosphate are incubated for an appropriate period of time in the presence of varying concentrations of a compound of the instant invention. The concentration of a sufficiently potent inhibitor (i.e., one that has a Ki substantially smaller than the concentration of enzyme in the assay vessel) required to inhibit the enzymatic activity of the sample by 50% is approximately equal to half of the concentration of the enzyme in that particular sample.

EXAMPLES

Examples provided are intended to assist in a further understanding of the invention. Particular materials employed, species and conditions are intended to be further illustrative of the invention and not limitative of the reasonable scope thereof.

EXAMPLE 1

(±)-4-(2-Butynyl)-1-(3-chlorophenyl)-3-[1-(4-cyanobenzyl)-5-imidazolylmethyl]-2-imidazolidinone hydrochloride Step A: Preparation of 1-triphenylmethyl-4-(hydroxymethyl)imidazole To a solution of 4-(hydroxymethyl)imidazole hydrochloride (35 g) in 250 mL of dry DMF at room temperature was added triethylamine (90.6 mL). A white solid precipitated from the solution. Chlorotriphenylmethane (76.1 g) in 500 mL of DMF was added dropwise. The reaction mixture was stirred for 20 hours, poured over ice, filtered, and washed with ice water. The resulting product was slurried with cold dioxane, filtered, and dried in vacuo to provide the titled product as a white solid which was sufficiently pure for use in the next step.

Step B: Preparation of 1-triphenylmethyl-4-(acetoxymethyl) imidazole

Alcohol from Step A was suspended in 500 mL of pyridine. Acetic anhydride (74 mL) was added dropwise, and the reaction was stirred for 48 hours during which it became homogeneous. The solution was poured into 2 L of EtOAc, washed with water (3×1 L), 5% aq. HCl soln. (2×1 L), sat. aq. NaHCO$_3$, and brine, then dried (Na$_2$SO$_4$), filtered, and concentrated in vacuo to provide the crude product. The acetate was isolated as a white powder (85.8 g) which was sufficiently pure for use in the next step.

Step C: Preparation of 1-(4-cyanobenzyl)-5-(acetoxymethyl)imidazole hydrobromide A solution of the product from Step B and α-bromo-p-tolunitrile (50.1 g) in 500 mL of EtOAc was stirred at 60° C. for 20 hours, during which a pale yellow precipitate formed. The reaction was cooled to room temperature and filtered to provide the solid imidazolium bromide salt. The filtrate was concentrated in vacuo to a volume 200 mL, reheated at 60° C. for two hours, cooled to room temperature, and filtered again. The filtrate was concentrated in vacuo to a volume 100 mL, reheated at 60° C. for another two hours, cooled to room temperature, and concentrated in vacuo to provide a pale yellow solid. All of the solid material was combined, dissolved in 500 mL of methanol, and warmed to 60° C. After two hours, the solution was reconcentrated in vacuo to provide a white solid which was triturated with hexane to remove soluble materials. Removal of residual solvents in vacuo provided the titled product hydrobromide as a white solid (50.4 g, 89% purity by HPLC) which was used in the next step without further purification.

Step D: Preparation of 1-(4-cyanobenzyl)-5-(hydroxymethyl)imidazole

To a solution of the acetate from Step C (50.4 g) in 1.5 L of 3:1 THF/water at 0° C. was added lithium hydroxide monohydrate (18.9 g). After one hour, the reaction was concentrated in vacuo, diluted with EtOAc (3 L), and washed with water, sat. aq. NaHCO$_3$ and brine. The solution was then dried (Na$_2$SO$_4$), filtered, and concentrated in vacuo to provide the crude product (26.2 g) as a pale yellow fluffy solid which was sufficiently pure for use in the next step without further purification.

Step E: Preparation of 1-(4-cyanobenzyl)-5-imidazolecarboxaldehyde

To a solution of the alcohol from Step D (21.5 g) in 500 mL of DMSO at room temperature was added triethylamine (56 mL), then SO$_3$-pyridine complex (40.5 g). After 45 minutes, the reaction was poured into 2.5 L of EtOAc, washed with water (4×1 L) and brine, dried (Na$_2$SO$_4$), filtered, and concentrated in vacuo to provide the titled aldehyde (18.7 g) as a white powder which was sufficiently pure for use in the next step without further purification.

Step F: Preparation of 1-(methanesulfonyl)-2-butyne

To a solution of 2-butynol (10.0 mL, 134 mmol) in 200 mL of dichloromethane at 0° C. was added methanesulfonyl chloride (23.4 g, 134 mmol), followed by dropwise addition of diisopropylethylamine (30 mL, 174 mmol). After 1.5 hours, the solution was poured into 0.5N KHSO$_4$ soln. and the organic layer was washed with brine. The solution was dried over Na$_2$SO$_4$, filtered, and concentrated in vacuo to provide the titled product (13.22 g).

Step G: Preparation of (±)-ethyl 2-|(phenylmethyl)imino|-4-hexynoate

To a solution of glycine ethyl ester hydrochloride (10.11 g, 72.4 mmol) in 200 mL of dichloromethane was added benzaldehyde (7.36 mL, 72.4 mmol), triethylamine (20.0 mL, 143 mmol), and magnesium sulfate (6 g). The solution was stirred at room temperature for 16 hours, filtered through a glass frit, and concentrated in vacuo. The residue was partitioned between ether and water, and the organic layer was washed with brine. The solution was dried over Na$_2$SO$_4$, filtered, and concentrated in vacuo to provide a pale yellow oil. A portion of this oil (9.90 g, 51.8 mmol) was dissolved in 200 mL of THF and cooled to −78° C. under nitrogen atmosphere. A solution of potassium tert-butoxide in THF (51.8 mL of 1M, 51.8 mmol) was added dropwise to produce a bright red solution. After 20 minutes, a solution of the mesylate from Step F (8.05 g, 54.4 mmol) in 20 mL of THF was added dropwise via cannula, and the solution was allowed to warm to room temperature. After 2 hours, the reaction was poured into EtOAc and washed with sat. NaHCO$_3$ soln. and brine, dried (Na$_2$SO$_4$), filtered, and concentrated in vacuo to provide the titled product.

Step H: Preparation of (±)-ethyl 2-|(tert-butoxycarbonyl)amino|-4-hexynoate

A solution of the product from Step G (ca. 51.8 mmol) was stirred at room temperature in 5% aqueous HCl solution (100 mL). After 12 hours, the solution was concentrated in vacuo to give an orange oil. This product was taken up in 50 mL of THF and sat. NaHCO$_3$ soln. was added (50 mL), followed by di-tert-butylpyrocarbonate (11.3 g, 51.8 mmol) at room temperature. After 6 hours, the reaction was poured into EtOAc and washed with sat. NaHCO$_3$ soln. and brine, dried (Na$_2$SO$_4$), filtered, and concentrated in vacuo to provide the titled product.

Step I: Preparation of (±)-2-|(tert-butoxycarbonyl)amino|-4-hexynoic acid

To a solution of the product from Step H (ca. 51.8 mmol) in THF (100 mL) and water (20 mL) was added at 0° C. a solution of lithium hydroxide monohydrate (6.5 g, 155 mmol). The solution was stirred for 1 hour at 0° C., then warmed to room temperature. After 48 hours, the solution was concentrated in vacuo. The aqueous mixture was extracted with EtOAc, acidified at 0° C. with 10% aq. HCl soln., then extracted with three portions of dichloromethane. The combined dichloromethane extracts were dried (Na$_2$SO$_4$), filtered, and concentrated in vacuo to provide the titled product as an orange oil (10.58 g).

Step J: Preparation of (±)-2-(tert-butoxycarbonylamino)-N-methoxy-N-methyl-4-hexynamide The product from Step I (10.58 g, 46.6 mmol), N,O-dimethylhydroxylamine hydrochloride (9.09 g, 93.2 mmol), HOBT hydrate (9.44 g, 69.9 mmol) and triethylamine (13.0 mL, 93.2 mmol) were stirred in dry DMF (150 mL) at 0° C. under nitrogen. EDC hydrochloride (11.5 g, 60.6 mmol) was added, and the reaction was stirred for 3 hours. The solution was partitioned between 2:1 ethyl acetate:hexane and water, washed with water, 10% aq. HCl, sat. NaHCO$_3$ soln and brine, then dried with sodium sulfate. The solvent was removed in vacuo to give the title compound (11.10 g, 88 % yield) as an orange oil Step K: Preparation of (±)-2-(tert-butoxycarbonylamino)-4-hexynal A suspension of lithium aluminum hydride (1.56 g, 41.1 mmol) in ether (150 mL) was stirred at room temperature for 30 minutes. The solution was cooled to −55° C. under nitrogen, and a solution of the product from Step J (11.10 g, 41.1 mmol) in ether (150 mL) was added over 15 min, maintaining the temperature below −50° C. When the addition was complete, the reaction was warmed to 5° C., then recooled to −40° C. A solution of potassium hydrogen sulfate (21.8 g) in 25 mL water was slowly added, maintaining the temperature below −35° C. The mixture was warmed to room temperature and stirred for one hour, filtered through Celite, and concentrated in vacuo to provide the title aldehyde.

Step L: Preparation of (±)-2-(tert-butoxycarbonylamino)-N-(3-chlorophenyl)-4-hexynamine To a 0° C. solution of 3-chloroaniline (4.33 mL, 40.9 mmol), the product from Step K (ca. 41 mmol), and crushed 4 Å molecular sieves (10 g) in dichloroethane (100 mL) under nitrogen was added sodium triacetoxyborohydride (12.9 g, 61.5 mmol). The reaction was stirred for one hour, then warmed to room temperature. After 3 hours, the solution was poured into EtOAc and washed with water, sat. NaHCO$_3$ soln. and brine. The solution was dried over sodium sulfate and concentrated in vacuo to provide the crude product.

Step M: Preparation of (±)-2-|(1-(4-cyanobenzyl)-5-imidazolylmethyl)amino|-1-|(3-chlorophenyl)amino|-4-hexyne To a solution of the product from Step L (2.74 g, 8.51 mmol) in 15 mL of dichloromethane was added at 0° C. dropwise 7 mL of trifluoroacetic acid. The reaction was allowed to gradually warm to room temperature. After 4 hours, the solution was concentrated in vacuo. The resulting product was partitioned between dilute aqueous NaHCO$_3$ solution and dichloromethane. The aqueous layer was washed with three portions of CH$_2$Cl$_2$, and the combined organics were dried (Na$_2$SO$_4$), filtered, and concentrated in vacuo to provide the free amine. To a solution of the amine (235 mg, 1.06 mmol) in 5 mL of 1,2-dichloroethane at 0° C. was added 4 Å powdered molecular sieves (350 mg), followed by sodium triacetoxyborohydride (285 mg, 1.35 mmol). The aldehyde from Step E (250 mg, 1.18 mmol) was added, and the reaction was stirred at 0° C. After 24 hours, , the reaction was poured into EtOAc, washed with sat. aq. NaHCO$_3$, and the aqueous layer was extracted with EtOAc. The combined organics were washed with brine, dried (Na$_2$SO$_4$), filtered, and concentrated in vacuo. The resulting product was taken up in 10 mL of 3:1 benzene:CH$_2$Cl$_2$, and propylamine (0.5 mL) was added. The reaction was stirred for 4 hours, then concentrated in vacuo, and purified by silica gel chromatography (30–75% acetone/hexane) to provide the titled compound.

Step N: Preparation of (±)-4-(2-butynyl)-1-(3-chlorophenyl)-3-|1-(4-cyanobenzyl)-5-imidazolylmethyl|-2-imidazolidinone hydrochloride To a solution of the product from Step M (75 mg, 0.14 mmol) in 1.0 mL of THF at 0° C. was added triethylamine (0.12 mL, 0.89 mmol), followed by triphosgene (26 mg, 0.088 mmol). The reaction was stirred at 0° C. for two hours, then poured into EtOAc and washed with sat. aq. NaHCO$_3$ and brine. The solution was dried (Na$_2$SO$_4$), filtered, and concentrated in vacuo. The product was purified by silica gel chromatography (50–75% acetone/hexane), taken up in

33

$CH_2Cl_2$ and treated with 1M HCl/ether solution, and concentrated in vacuo. The titled product hydrochloride (14 mg) was isolated as an orange powder.

FAB mass spectrum m/e 444 (M+1).

Analysis calculated for $C_{25}H_{22}ClN_5O \bullet 1.0\ HCl \bullet 1.60\ H_2O$: C, 58.97; H, 5.19; N, 13.75; Found: C, 59.06; H, 5.27; N, 12.49.

EXAMPLE 2

(S)-4-n-Butyl-3-[1-(4-cyanobenzyl)-5-imidazolylmethyl]-1-(2,3-dimethylphenyl)-2-imidazolidinone hydrochloride Step A: N-Methoxy-N-methyl 2(S)-(tert-butoxycarbonylamino)hexanamide 2(S)-Butoxycarbonylaminohexanoic acid (24.6 g, 0.106 mol), N,O-dimethylhydroxylamine hydrochloride (15.5 g, 0.15 mol), EDC hydrochloride (22.3 g, 0.117 mol) and HOBT (14.3 g, 0.106 mol) were stirred in dry, degassed DMF (300 mL) at 20° C. under nitrogen. N-Methylmorpholine was added to obtain pH 7. The reaction was stirred overnight, the DMF distilled under high vacuum, and the residue partitioned between ethyl acetate and 2% potassium hydrogen sulfate. The organic phase was washed with saturated sodium bicarbonate, water, and saturated brine, and dried with magnesium sulfate. The solvent was removed in vacuo to give the title compound.

Step B: 2(S)-(tert-Butoxycarbonylamino)hexanal

A mechanically stirred suspension of lithium aluminum hydride (5.00 g, 0.131 mol) in ether (250 mL) was cooled to −45° C. under nitrogen. A solution of the product from Step A (28.3 g, 0.103 mol) in ether (125 mL) was added, maintaining the temperature below −35° C. When the addition was complete, the reaction was warmed to 5° C., then recooled to −45° C. A solution of potassium hydrogen sulfate (27.3 g, 0.200 mol) in water was slowly added, maintaining the temperature below −5° C. After quenching, the reaction was stirred at room temperature for 1 h. The mixture was filtered through Celite, the ether evaporated, and the remainder partitioned between ethyl acetate and 2% potassium hydrogen sulfate. After washing with saturated brine, drying over magnesium sulfate and solvent removal, the title compound was obtained.

Step C: N-(2,3-Dimethylphenyl)-2(S)-(tert-butoxycarbonylamino)hexanamine 2,3-Dimethylaniline (8.32 mL, 68.3 mmol) was dissolved in dichloroethane under nitrogen. Acetic acid was added to obtain pH 5, and sodium triacetoxyborohydride (17.2 g, 80.8 mmol) and crushed molecular sieves (4 g) were added. A solution of the product from Step B (13.3 g, 62.1 mmol) in dichloroethane (80 mL) was added slowly dropwise at 20° C. The reaction was stirred overnight, then quenched with saturated sodium bicarbonate solution. The aqueous layer was removed, the organic phase washed with saturated brine and dried over magnesium sulfate. Crystallization from hexane gave the title compound.

Step D: Preparation of (S)-2-[(1-(4-cyanobenzyl)-5-imidazolylmethyl)amino]-1-[(2,3-dimethylphenyl)amino]-4-hexane To a solution of the product from Step C (581 mg, 1.81 mmol) in 5 mL of dichloromethane was added at room temperature dropwise 2.5 mL of trifluoroacetic acid. After one hour, the solution was concentrated in vacuo. The resulting product was reconcentrated from benzene three times to remove excess trifluoroacetic acid. To a solution of the amine salt in 5 mL of 1,2-dichloroethane at 0° C. was added 4 Å powdered molecular sieves, followed by sodium triacetoxyborohydride (961 mg, 4.53 mmol). The aldehyde from Step E of Example 1 (421 mg, 1.99 mmol) was added

34 at 0° C., and the reaction was stirred overnight, allowing it to warm to room temperature. The reaction was poured into EtOAc, washed with sat. aq. $NaHCO_3$, and the aqueous layer was extracted with EtOAc. The combined organics were washed with brine, dried ($Na_2SO_4$), filtered, and concentrated in vacuo. The resulting product was taken up in 6 mL of 5:1 benzene:$CH_2Cl_2$, and propylamine (1 mL) was added. The reaction was stirred overnight, then concentrated in vacuo, and purified by silica gel chromatography (5% MeOH/$CH_2Cl_2$) to provide the titled compound.

Step E: Preparation of (S)-4-n-butyl-3-[1-(4-cyanobenzyl)-5-imidazolylmethyl]-1-(2,3-dimethylphenyl)-2-imidazolidinone hydrochloride To a solution of the product from Step D (222 mg, 0.524 mmol) in 3.7 mL of THF at 0° C. was added triethylamine (0.46 mL, 3.3 mmol), followed by triphosgene (96 mg, 0.33 mmol). The reaction was stirred at 0° C. for one hour, then poured into EtOAc and washed with sat. aq. $NaHCO_3$ and brine. The solution was dried ($Na_2SO_4$), filtered, and concentrated in vacuo. The product was purified by silica gel chromatography (2.5% MeOH/$CH_2Cl_2$) to yield ca. 80 mg of an impure product. The product was taken up in methanol and injected onto a preparative HPLC column and purified with a mixed gradient of 25%–55% acetonitrile/0.1% TFA; 75%–45% 0.1% aqueous TFA over 50 minutes. After concentration in vacuo, the resultant product was partitioned between dichloromethane and aq. $NaHCO_3$ soln., and the aqueous phase was extracted with $CH_2Cl_2$. The organic solution was washed with brine, dried ($Na_2SO_4$), filtered, and concentrated to dryness to provide the product free base, which was taken up in $CH_2Cl_2$ and treated with excess 1M HCl/ether solution. After concentrated in vacuo, the titled product (33.7 mg) was isolated as a white powder.

FAB mass spectrum m/e 442 (M+1).

Analysis calculated for $C_{27}H_{31}N_5O \bullet 1.90\ HCl$: C, 63.53; H, 6.50; N, 13.72; Found: C, 63.78; H, 7.14; N, 11.74.

EXAMPLE 3

1-(3-Chlorophenyl)-3-[1-(4-cyanobenzyl)-5-imidazolylmethyl]-2-imidazolidinone hydrochloride Step A: Preparation of N-(2-aminoethyl)-3-chloroaniline hydrochloride To a solution of 3-chloroaniline (30 mL) in 500 mL of dichloromethane at 0° C. was added dropwise a solution of 4N HCl in 1,4-dioxane (80 mL). The solution was warmed to room temperature, then concentrated to dryness in vacuo to provide a white powder. A mixture of this powder with 2-oxazolidinone (24.6 g) was heated under nitrogen atmosphere at 160° C. for 10 hours, during which the solids melted, and gas evolution was observed. The reaction was allowed to cool, forming the titled compound as a pale brown solid.

Step B: Preparation of N-[1-(4-cyanobenzyl)-5-imidazolylmethyl]-N'-(3-chlorophenyl)ethylenediamine The amine hydrochloride from Step A (978 mg) was partitioned between dilute aqueous $NaHCO_3$ solution and methylene chloride. The aqueous layer was washed with three portions of $CH_2Cl_2$, and the combined organics were dried ($Na_2SO_4$), filtered, and concentrated in vacuo to provide the free amine. To a solution of the amine in 11 mL of 1,2-dichloroethane at 0° C. was added 4 Å powdered molecular sieves (2 g), followed by sodium triacetoxyborohydride (3.04 g). The aldehyde from Step E of Example 1 (1.21 g) was added, and the reaction was stirred at 0° C. After 15 hours, , the reaction was poured into EtOAc, washed with sat. aq. $NaHCO_3$, and the aqueous layer was extracted with EtOAc. The combined organics were washed with brine, dried (Na$_2$SO$_4$), filtered, and concentrated in vacuo. The resulting product was taken up in 60 mL of 5:1 benzene:CH$_2$Cl$_2$, and propylamine (10 mL) was added. The reaction was stirred for 12 hours, then concentrated in vacuo, and purified by silica gel chromatography (5% MeOH/CHCl$_3$) to provide the titled compound (1.33 g) as a white foam.

Step C: Preparation of 1-(3-chlorophenyl)-3-|1-(4-cyanobenzyl)-5-imidazolylmethyl|-2-imidazolidinone hydrochloride To a solution of the product from Step B (500 mg, 1.37 mmol) in 9.6 mL of THF at 0° C. was added triethylamine (1.2 mL, 8.6 mmol), followed by triphosgene (251 mg, 0.847 mmol). The reaction was stirred at 0° C. for one hour, then poured into EtOAc and washed with sat. aq. NaHCO$_3$ and brine. The solution was dried (Na$_2$SO$_4$), filtered, and concentrated in vacuo. The product was purified by silica gel chromatography (2.5–5% MeOH/CH$_2$Cl$_2$), then taken up in methanol and injected onto a preparative HPLC column and purified with a mixed gradient of 25%–55% acetonitrile/ 0.1% TFA; 75%–45% 0.1% aqueous TFA over 50 minutes. After concentration in vacuo, the resultant product was partitioned between dichloromethane and aq. NaHCO$_3$ soln., and the aqueous phase was extracted with CH$_2$Cl$_2$. The organic solution was washed with brine, dried (Na$_2$SO$_4$), filtered, and concentrated to dryness to provide the product free base, which was taken up in CH$_2$Cl$_2$ and treated with excess 1M HCl/ether solution. After concentrated in vacuo, the titled product (57.3 mg) was isolated as a white powder.

FAB mass spectrum m/e 392 (M+1).

Analysis calculated for C$_{21}$H$_{18}$N$_5$OCl•1.40 HCl•0.50 H$_2$O: C, 55.84; H, 4.55; N, 15.50; Found: C, 55.93; H, 4.56; N, 14.81.

EXAMPLE 4

4-(S)-4-n-Butyl-3-|4-chloro-1-(4-cyanobenzyl)-5-imidazolylmethyl|-1-(2-chloro-5,6-dimethylphenyl)-2-imidazolidinone hydrochloride Step A: Preparation of (S)-2-|(4-chloro-1-(4-cyanobenzyl)-5-imidazolylmethyl)amino|-1-|(2-chloro-5,6-dimethylphenyl)amino|-4-hexane hydrochloride To a solution of the product from Step D of Example 2 (213 mg, 0.502 mmol) in 2.8 mL of THF was added at −78° C. sulfuryl chloride (0.044 mL, 0.55 mmol). The reaction was allowed to warm to room temperature. After one hour, an additional portion of sulfuryl chloride (0.011 mL) was added, and the reaction was stirred overnight, then poured into EtOAc and washed with sat. aq. NaHCO$_3$ and brine. The solution was dried (Na$_2$SO$_4$), filtered, and concentrated in vacuo. The product was taken up in methanol and injected onto a preparative HPLC column and purified with a mixed gradient of 25%–55% acetonitrile/0.1% TFA; 75%–45% 0.1% aqueous TFA over 50 minutes. After concentration in vacuo, the resultant product was partitioned between dichloromethane and aq. NaHCO$_3$ soln., and the aqueous phase was extracted with CH$_2$Cl$_2$. The organic solution was washed with brine, dried (Na$_2$SO$_4$), filtered, and concentrated to dryness to provide the product free base, which was taken up in CH$_2$Cl$_2$ and treated with excess 1M HCl/ether solution. After concentrated in vacuo, the titled product was isolated as a white powder.

Step B: Preparation of 4-(S)-4-n-butyl-3-|4-chloro- 1-(4-cyanobenzyl)-5-imidazolylmethyl|-1-(2-chloro-5,6-dimethylphenyl)-2-imidazolidinone hydrochloride To a solution of the product from Step A (49 mg, 0.10 mmol) in 1 mL of THF at 0° C. was added triethylamine (0.089 mL, 0.64 mmol), followed by triphosgene (19 mg, 0.063 mmol). The reaction was stirred at 0° C. for one hour. An additional portion of triphosgene (5 mg) was added, and the reaction was stirred for 15 minutes, then poured into EtOAc and washed with sat. aq. NaHCO$_3$ and brine. The solution was dried (Na$_2$SO$_4$), filtered, and concentrated in vacuo. The product was purified by silica gel chromatography (2.5–5% MeOH/CH$_2$Cl$_2$), then taken up in CH$_2$Cl$_2$ and treated with excess 1M HCl/ether solution. After concentrated in vacuo, the titled product (18 mg) was isolated as a white powder.

FAB mass spectrum m/e 510 (M+1).

Analysis calculated for C$_{27}$H$_{29}$N$_5$OCl$_2$•1.0 HCl•0.30 H$_2$O: C, 58.71; H, 5.58; N, 12.68; Found: C, 58.75; H, 5.72; N, 11.10.

EXAMPLE 5

(S)-1-(3-Chlorobenzyl)-3-|1-(4-cyanobenzyl)-5-imidazolylmethyl|-4-|(2-methanesulfonyl)ethyl|-2-imidazolidinone hydrochloride Step A: Preparation of (S)-2-(tert-butoxycarbonylamino)-N-methoxy-N-methyl-4-(methylthio)butanamide L-N-Boc-methionine (30.0 g, 0.120 mol), N,O-dimethylhydroxylamine hydrochloride (14.1 g, 0.144 mol), EDC hydrochloride (27.7 g, 0.144 mol) and HOBT (19.5 g, 0.144 mol) were stirred in dry DMF (300 mL) at 20° C. under nitrogen. More N,O-dimethylhydroxylamine hydrochloride (2.3 g, 23 mmol) was added to obtain pH 7–8. The reaction was stirred overnight, the DMF distilled to half the original volume under high vacuum, and the residue partitioned between ethyl acetate and sat. NaHCO$_3$ soln. The organic phase was washed with saturated sodium bicarbonate, water, 10% citric acid, and brine, and dried with sodium sulfate. The solvent was removed in vacuo to give the titled compound (39.8 g).

Step B: Preparation of (S)-2-(tert-butoxycarbonylamino)-N-methoxy-N-methyl-4-(methanesulfonyl)butanamide To solution of the product from Step A (23.1 g, 79.2 mmol) in methanol (300 mL) at 0° C. was added a suspension of magnesium monoperoxyphthalate (117 g, 238 mmol) in 500 mL MeOH. The reaction was allowed to warm to room temperature. After 16 hours, the reaction was quenched at 0° C. by the addition of 2N Na$_2$S$_2$O$_3$ soln. The solution was poured into EtOAc and sat NaHCO$_3$ solution, and the organic layer was washed with brine, dried (Na$_2$SO$_4$), filtered, and concentrated in vacuo to provide the crude titled compound (23.9 g, 93% yield).

Step C: Preparation of (S)-2-(tert-butoxycarbonylamino)-4-(methanesulfonyl)butanal A suspension of lithium aluminum hydride (5.15 g, 0.136 mol) in ether (290 mL) was stirred at room temperature for one hour. The solution was cooled to −75° C. under nitrogen, and a solution of the product from Step B (23.9 g, 73.6 mol) in THF (60 mL) was added over ca. 30 min, maintaining the temperature below −40° C. When the addition was complete, the reaction was warmed to −15° C., then recooled to −35° C. A solution of potassium hydrogen sulfate (19.4 g) in 77 mL water was slowly added. The mixture was warmed to room temperature, and stirred for one hour. The solution was filtered through a pad of celite, washed with 10% HCl solution, sat. NaHCO$_3$ solution and brine, dried (Na$_2$SO$_4$), filtered, and concentrated in vacuo to provide the titled aldehyde (7.44 g).

Step D: Preparation of (S)-2-(tert-butoxycarbonylamino)-N-(3-chlorobenzyl)-4-(methanesulfonyl)butanamine To a solution of 3-chlorobenzylamine (0.628 mL, 5.14 mmol) and crushed molecular sieves (1.5 g) in dichloroethane (10 mL) under nitrogen at 0° C. was added sodium triacetoxyborohydride (2.73 g, 12.9 mmol), followed the product from Step C (2.73 g, 5.14 mmol). The reaction was stirred overnight, allowing it to warm to room temperature. The solution was poured into EtOAc and sat NaHCO$_3$ solution, and the organic layer was washed with brine, dried (Na$_2$SO$_4$), filtered, and concentrated in vacuo to provide the crude product which was purified by silica gel chromatography (2.5–5% MeOH/CHCl$_3$) to obtain the titled compound (1.53 g) as a white foam.

Step E: Preparation of (S)-2-(tert-butoxycarbonylamino)-N-(benzyloxycarbonyl)-N-(3-chlorobenzyl)-4-(methanesulfonyl)butanamine To a solution of the amine from Step D (754 mg, 1.93 mmol) and triethylamine (0.403 mL, 2.89 mmol) in 5 mL of dichloromethane at 0° C. was added benzylchloroformate (0.303 mL, 2.12 mmol). After 2 hours, the solution was poured into EtOAc and sat NH$_4$Cl solution, and the organic layer was washed with sat. NaHCO$_3$ soln. and brine, dried (Na$_2$SO$_4$), filtered, and concentrated in vacuo to provide the crude product which was purified by silica gel chromatography (30–40% EtOAc/hexane) to obtain the titled compound (360 mg) as a white foam.

Step F: Preparation of (S)-2-|(1-(4-cyanobenzyl)-5-imidazolylmethyl)amino|-N-(benzyloxycarbonyl)-N-(3-chlorobenzyl)-4-(methanesulfonyl)butanamine To a solution of the product from Step E (360 mg, 0.686 mmol) in 6 mL of dichloromethane was added at room temperature dropwise 3 mL of trifluoroacetic acid. After 30 minutes, the solution was concentrated in vacuo. The resulting product was reconcentrated from benzene three times to remove excess trifluoroacetic acid. To a solution of the amine salt in 4.2 mL of 1,2-dichloroethane at 0° C. was added 4 Å powdered molecular sieves, followed by sodium triacetoxyborohydride (363 mg, 1.71 mmol). The aldehyde from Step E of Example 1 (159 mg, 0.754 mmol) was added at 0° C., followed by N-methylmorpholine (0.076 mL, 0.69 mmol). The reaction was stirred overnight, allowing it to warm to room temperature. The reaction was poured into EtOAc, washed with sat. aq. NaHCO$_3$ and brine, dried (Na$_2$SO$_4$), filtered, and concentrated in vacuo. The resulting product was purified by silica gel chromatography (50–75% acetone/hexane) to provide the titled compound (250 mg).

Step G: Preparation of (S)-2-|(1-(4-cyanobenzyl)-5-imidazolylmethyl)amino|-N-(3-chlorobenzyl)-4-(methanesulfonyl)butanamine To a solution of the product from Step F (163 mg, 0.262 mmol) in 3 mL of methanol and 3 mL of EtOAc was added at room temperature 10% palladium on carbon (10 mg). A balloon of hydrogen gas was introduced to the solution via syringe needle, and the reaction was stirred for ca. 20 minutes. The solution was filtered through celite to remove the catalyst, then concentrated in vacuo. The resulting product was purified by silica gel chromatography (4% MeOH/CH$_2$Cl$_2$ with 1% NH$_4$OH) to provide the titled compound (63 mg).

Step H: Preparation of (S)-1-(3-chlorobenzyl)-3-|1-(4-cyanobenzyl)-5-imidazolylmethyl|-4-|(2-methanesulfonyl)ethyl|-2-imidazolidinone hydrochloride To a solution of the product from Step G (63 mg, 0.17 mmol) in 2.5 mL of THF at 0° C. was added triethylamine (0.15 mL, 1.0 mmol), followed by triphosgene (31 mg, 0.10 mmol). The reaction was stirred at 0° C. for 1.5 hour, then poured into EtOAc and washed with sat. aq. NaHCO$_3$ and brine. The solution was dried (Na$_2$SO$_4$), filtered, and concentrated in vacuo. The product was taken up in methanol and injected onto a preparative HPLC column and purified with a mixed gradient of 25%–55% acetonitrile/0.1% TFA; 75%–45% 0.1% aqueous TFA over 50 minutes. After concentration in vacuo, the resultant product was partitioned between dichloromethane and aq. NaHCO$_3$ soln., and the aqueous phase was extracted with CH$_2$Cl$_2$. The organic solution was washed with brine, dried (Na$_2$SO$_4$), filtered, and concentrated to dryness to provide the product free base, which was taken up in CH$_2$Cl$_2$ and treated with excess 1M HCl/ether solution. After concentrated in vacuo, the titled product (9.3 mg) was isolated as a white powder.

FAB mass spectrum m/e 512 (M+1).

Analysis calculated for C$_{25}$H$_{26}$N$_5$O$_3$SCl•HCl: C, 54.75; H, 4.96; N, 12.77; Found: C, 56.31; H, 5.67; N, 11.38.

EXAMPLE 6

In vitro inhibition of ras farnesyl transferase

*Assays of farnesyl-protein transferase.* Partially purified bovine FPTase and Ras peptides (Ras-CVLS, Ras-CVIM and Ras-CAIL) were prepared as described by Schaber et al., *J. Biol. Chem.* 265:14701–14704 (1990), Pompliano, et al., *Biochemistry* 31:3800 (1992) and Gibbs et al., *PNAS U.S.A.* 86:6630–6634 (1989), respectively. Bovine FPTase was assayed in a volume of 100 µl containing 100 mM N-(2-hydroxy ethyl) piperazine-N'-(2-ethane sulfonic acid) (HEPES), pH 7.4, 5 mM MgCl$_2$, 5 mM dithiothreitol (DTT), 100 mM [$^3$H]-farnesyl diphosphate ([$^3$H]-FPP: 740 CBq/mmol, New England Nuclear), 650 nM Ras-CVLS and 10 µg/ml FPTase at 31° C. for 60 min. Reactions were initiated with FPTase and stopped with 1 ml of 1.0M HCL in ethanol. Precipitates were collected onto filter-mats using a TomTec Mach II cell harvester, washed with 100% ethanol, dried and counted in an LKB β-plate counter. The assay was linear with respect to both substrates, FPTase levels and time; less than 10% of the [$^3$H]-FPP was utilized during the reaction period. Purified compounds were dissolved in 100% dimethyl sulfoxide (DMSO) and were diluted 20-fold into the assay. Percentage inhibition is measured by the amount of incorporation of radioactivity in the presence of the test compound when compared to the amount of incorporation in the absence of the test compound.

Human FPTase was prepared as described by Omer et al, *Biochemistry* 32:5167–5176 (1993). Human FPTase activity was assayed as described above with the exception that 0.1% (w/v) polyethylene glycol 20,000, 10 µM ZnCl$_2$ and 100 nM Ras-CVIM were added to the reaction mixture. Reactions were performed for 30 min., stopped with 100 µl of 30% (v/v) trichloroacetic acid (TCA) in ethanol and processed as described above for the bovine enzyme.

The compound of the instant invention described hereinabove in Example 1 was tested for inhibitory activity against human FPTase by the assay described above and was found to have IC$_{50}$ of <10 µM.

EXAMPLE 7

In vivo ras farnesylation assay

The cell line used in this assay is a v-ras line derived from either Rat1 or NIH3T3 cells, which expressed viral Ha-ras p21. The assay is performed essentially as described in DeClue, J. E. et al., *Cancer Research* 51:712–717, (1991). Cells in 10 cm dishes at 50–75% confluency are treated with the test compound (final concentration of solvent, methanol or dimethyl sulfoxide, is 0.1%). After 4 hours at 37° C., the cells are labelled in 3 ml methionine-free DMEM supplemeted with 10% regular DMEM, 2% fetal bovine serum and 400 mCi[$^{35}$S]methionine (1000 Ci/mmol). After an additional 20 hours, the cells are lysed in 1 ml lysis buffer (1%

NP40/20 mM HEPES, pH 7.5/5 mM MgCl$_2$/1 mM DTT/10 mg/ml aprotinen/2 mg/ml leupeptin/2 mg/ml antipain/0.5 mM PMSF) and the lysates cleared by centrifugation at 100,000×g for 45 min. Aliquots of lysates containing equal numbers of acid-precipitable counts are bought to 1 ml with IP buffer (lysis buffer lacking DTT) and immunoprecipitated with the ras-specific monoclonal antibody Y13-259 (Furth, M. E. et al., *J. Virol.* 43:294–304, (1982)). Following a 2 hour antibody incubation at 4° C., 200 ml of a 25% suspension of protein A-Sepharose coated with rabbit anti rat IgG is added for 45 min. The immunoprecipitates are washed four times with IP buffer (20 nM HEPES, pH 7.5/1 mM EDTA/1% Triton X-100,0.5% deoxycholate/0.1%/ SDS/0.1M NaCl) boiled in SDS-PAGE sample buffer and loaded on 13% acrylamide gels. When the dye front reached the bottom, the gel is fixed, soaked in Enlightening, dried and autoradiographed. The intensities of the bands corresponding to farnesylated and nonfarnesylated ras proteins are compared to determine the percent inhibition of farnesyl transfer to protein.

EXAMPLE 8

In vivo growth inhibition assay

To determine the biological consequences of FPTase inhibition, the effect of the compounds of the instant invention on the anchorage-independent growth of Rat1 cells transformed with either a v-ras, v-raf, or v-mos oncogene is tested. Cells transformed by v-Raf and v-Mos maybe included in the analysis to evaluate the specificity of instant compounds for Ras-induced cell transformation.

Rat 1 cells transformed with either v-ras, v-raf, or v-mos are seeded at a density of 1×10$^4$ cells per plate (35 mm in diameter) in a 0.3% top agarose layer in medium A (Dulbecco's modified Eagle's medium supplemented with 10% fetal bovine serum) over a bottom agarose layer (0.6%). Both layers contain 0.1% methanol or an appropriate concentration of the instant compound (dissolved in methanol at 1000 times the final concentration used in the assay). The cells are fed twice weekly with 0.5 ml of medium A containing 0.1% methanol or the concentration of the instant compound. Photomicrographs are taken 16 days after the cultures are seeded and comparisons are made.

What is claimed is:

1. A compound which inhibits farnesyl-protein transferase of the formula I:

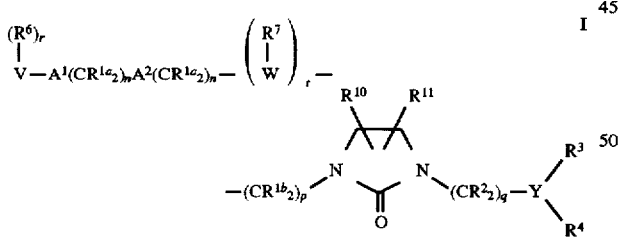

wherein:

$R^{1a}$, $R^{1b}$ and $R^2$ are independently selected from:

a) hydrogen, b) aryl, heterocycle, $C_3$–$C_{10}$ cycloalkyl, $C_2$–$C_6$ alkenyl, $C_2$–$C_6$ alkynyl, $R^8O$—, $R^9S(O)_m$—, $R^8C(O)NR^8$—, CN, NO$_2$, $(R^8)_2N$—$C(NR^8)$—, $R^8C(O)$—, $R^8OC(O)$—, N$_3$, —N($R^8)_2$, or $R^9OC(O)NR^8$—, c) $C_1$–$C_6$ alkyl unsubstituted or substituted by aryl, heterocyclic, $C_3$–$C_{10}$ cycloalkyl, $C_2$–$C_6$ alkenyl, $C_2$–$C_6$ alkynyl, $R^8O$—, $R^9S(O)_m$—, $R^8C(O)NR^8$—, CN, $(R^8)_2N$—$C(NR^8)$—, $R^8C(O)$—, $R^8OC(O)$—, N$_3$, —N($R^8)_2$, or $R^9OC(O)$—NR$^8$—;

$R^3$ and $R^4$ are independently selected from F, Cl, Br, N($R^8)_2$, CF$_3$, NO$_2$, $(R^8)O$—, $(R^9)S(O)_m$—, $(R^8)C(O)NH$—, H$_2$N—C(NH)—, $(R^8)C(O)$—, $(R^8)OC(O)$—, N$_3$, CN, CF$_3$(CH$_2$)$_n$O—, $(R^9)OC(O)NR^8$—, $C_1$–$C_{20}$ alkyl, substituted or unsubstituted aryl and substituted or unsubstituted heterocycle;

$R^6$ is independently selected from:

a) hydrogen, b) aryl, heterocycle, $C_3$–$C_{10}$ cycloalkyl, $C_2$–$C_6$ alkenyl, $C_2$–$C_6$ alkynyl, perfluoroalkyl, F, Cl, Br, $R^8O$—, $R^9S(O)_m$—, $R^8C(O)NR^8$—, CN, NO$_2$, $R^8_2N$—C(NR$^8$)—, $R^8C(O)$—, $R^8OC(O)$—, N$_3$, —N($R^8)_2$, or $R^9OC(O)NR^8$—, and c) $C_1$–$C_6$ alkyl unsubstituted or substituted by aryl, heterocycle, $C_3$–$C_{10}$ cycloalkyl, $C_2$–$C_6$ alkenyl, $C_2$–$C_6$ alkynyl, perfluoroalkyl, F, Cl, Br, $R^8O$—, $R^9S(O)_m$—, $R^8C(O)NH$—, CN, H$_2$N—C(NH)—, $R^8C(O)$—, $R^8OC(O)$—, N$_3$, —N($R^8)_2$, or $R^8OC(O)NH$—;

$R^7$ is selected from:

a) hydrogen, b) $C_2$–$C_6$ alkenyl, $C_2$–$C_6$ alkynyl, perfluoroalkyl, F, Cl, Br, $R^8O$—, $R^9S(O)_m$—, $R^8C(O)NR^8$—, CN, NO$_2$, $(R^8)_2N$—C—(NR$^8$)—, $R^8C(O)$—, $R^8OC(O)$—, N$_3$, —N($R^8)_2$, or $R^9OC(O)NR^8$—, and c) $C_1$–$C_6$ alkyl unsubstituted or substituted by perfluoroalkyl, F, Cl, Br, $R^8O$—, $R^9S(O)_m$—, $R^8C(O)NR^8$—, CN, $(R^8)_2N$—C(NR$^8$)—, $R^8C(O)$—, $R^8OC(O)$—, N$_3$, —N($R^8)_2$, or $R^9OC(O)NR^8$—;

$R^8$ is independently selected from hydrogen, $C_1$–$C_6$ alkyl, benzyl and aryl;

$R^9$ is independently selected from $C_1$–$C_6$ alkyl and aryl;

$R^{10}$ and $R^{11}$ are independently selected from: H;

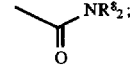

or $C_{1-5}$ alkyl, unbranched or branched, unsubstituted or substituted with one or more of:

1) aryl, 2) heterocycle,

3) OR$^8$,

4) SR$^9$, SO$_2$R$^9$, or

5)

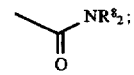

$A^1$ and $A^2$ are independently selected from: a bond, —CH=CH—, —C≡C—, —C(O)—, —C(O)NR$^8$—, —NR$^8$C(O)—, O, —N(R$^8$)—, —S(O)$_2$N(R$^8$)—, —N(R$^8$)S(O)$_2$—, or S(O)$_m$;

V is selected from:

a) hydrogen, b) heterocycle, c) aryl, d) $C_1$–$C_{20}$ alkyl wherein from 0 to 4 carbon atoms are replaced with a a heteroatom selected from O, S, and N, and e) $C_2$–$C_{20}$ alkenyl, provided that V is not hydrogen if $A^1$ is S(O)$_m$ and V is not hydrogen if $A^1$ is a bond, n is 0 and $A^2$ is S(O)$_m$;

W is a heterocycle;
Y is aryl or heteroaryl;
m is 0, 1 or 2;
n is 0, 1, 2, 3 or 4;
p is 0, 1, 2, 3 or 4;
q is 0, 1, 2, 3 or 4;
r is 0 to 5, provided that r is 0 when V is hydrogen; and
t is 0 or 1;
provided that when W is imidazolyl, then the substitutent $(R^6)_r$—V—$A^1(CR^{1a}{}_2)_nA^2(CR^{1a}{}_2)_n$— is not H, $C_1$–$C_6$ alkyl or a nitrogen protecting group;
or a pharmaceutically acceptable salt thereof.

2. A compound which inhibits farnesyl-protein transferase of the formula Ia:

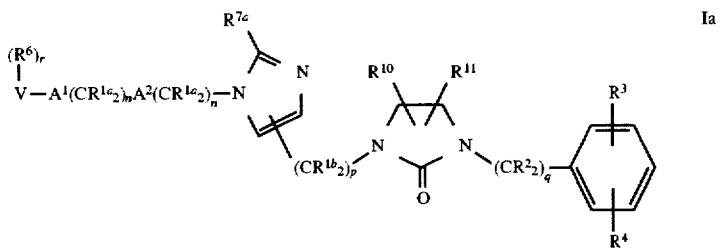

Ia wherein:
$R^{1a}$ and $R^2$ are independently selected from: hydrogen or $C_1$–$C_6$ alkyl;
$R^{1b}$ is independently selected from:
 a) hydrogen,
 b) aryl, heterocycle, cycloalkyl, $R^8O$—, —$N(R^8)_2$ or $C_2$–$C_6$ alkenyl,
 c) $C_1$–$C_6$ alkyl unsubstituted or substituted by aryl, heterocycle, cycloalkyl, alkenyl, $R^8O$—, or —$N(R^8)_2$;
$R^3$ and $R^4$ are independently selected from F, Cl, Br, $N(R^8)_2$, $CF_3$, $NO_2$, $(R^8)O$—, $(R^9)S(O)_m$—, $(R^8)C(O)NH$—, $H_2N$—C(NH)—, $(R^8)C(O)$—, $(R^8)OC(O)$—, $N_3$, CN, $(R^9)OC(O)NR^8$—, $C_1$–$C_{20}$ alkyl, substituted or unsubstituted aryl and substituted or unsubstituted heterocycle;
$R^6$ is independently selected from:
 a) hydrogen,
 b) $C_1$–$C_6$ alkyl, $C_2$–$C_6$ alkenyl, $C_2$–$C_6$ alkynyl, $C_1$–$C_6$ perfluoroalkyl, F, Cl, $R^8O$—, $R^8C(O)NR^8$—, CN, $NO_2$, $(R^8)_2N$—C($NR^8$)—, $R^8C(O)$—, $R^8OC(O)$—, —$N(R^8)_2$, or $R^9OC(O)NR^8$—, and
 c) $C_1$–$C_6$ alkyl substituted by $C_1$–$C_6$ perfluoroalkyl, $R^8O$—, $R^8C(O)NR^8$—, $(R^8)_2N$—C($NR^8$)—, $R^8C(O)$—, $R^8OC(O)$—, —$N(R^8)_2$, or $R^9OC(O)NR^8$—;
$R^{7a}$ is hydrogen or methyl;
$R^8$ is independently selected from hydrogen, $C_1$–$C_6$ alkyl, benzyl and aryl;
$R^9$ is independently selected from $C_1$–$C_6$ alkyl and aryl;
$R^{10}$ and $R^{11}$ are independently selected from: H;

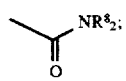

or $C_{1-5}$ alkyl, unbranched or branched, unsubstituted or substituted with one or more of:
 1) aryl,
 2) heterocycle,
 3) $OR^8$,
 4) $SR^9$, $SO_2R^9$, or

5)

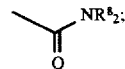

$A^1$ and $A^2$ are independently selected from: a bond, —CH=CH—, —C≡C—, —C(O)—, —C(O)$NR^8$—, O, —$N(R^8)$—, or $S(O)_m$;
V is selected from:
 a) hydrogen,
 b) heterocycle selected from pyrrolidinyl, imidazolyl, pyridinyl, thiazolyl, pyridonyl, 2-oxopiperidinyl, indolyl, quinolinyl, isoquinolinyl, and thienyl,
 c) aryl,
 d) $C_1$–$C_{20}$ alkyl wherein from 0 to 4 carbon atoms are replaced with a a heteroatom selected from O, S, and N, and
 e) $C_2$–$C_{20}$ alkenyl, and
provided that V is not hydrogen if $A^1$ is $S(O)_m$ and V is not hydrogen if $A^1$ is a bond, n is 0 and $A^2$ is $S(O)_m$;
m is 0, 1 or 2;
n is 0, 1, 2, 3 or 4;
p is 0, 1, 2, 3 or 4; and
q is 0, 1, 2, 3 or 4; and
r is 0 to 5, provided that r is 0 when V is hydrogen;
provided that the substitutent $(R^6)_r$—V—$A^1(CR^{1a}{}_2)_nA^2(CR^{1a}{}_2)_n$— is not H, $C_1$–$C_6$ alkyl or a nitrogen protecting group;
or a pharmaceutically acceptable salt thereof.

3. A compound which inhibits farnesyl-protein transferase of the formula Ib:

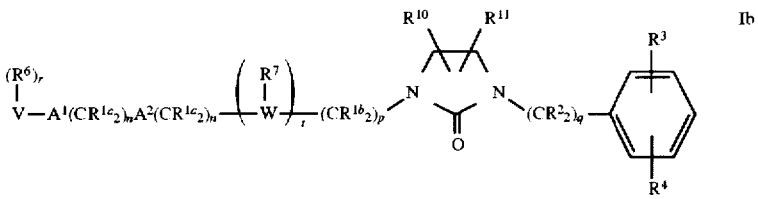

wherein:

$R^{1a}$ and $R^2$ are independently selected from: hydrogen or $C_1-C_6$ alkyl;

$R^{1b}$ is independently selected from:

a) hydrogen, b) aryl, heterocycle, cycloalkyl, $R^8O$—, —$N(R^8)_2$ or $C_2-C_6$ alkenyl, c) $C_1-C_6$ alkyl unsubstituted or substituted by aryl, heterocycle, cycloalkyl, alkenyl, $R^8O$—, or —$N(R^8)_2$;

$R^3$ and $R^4$ are independently selected from F, Cl, Br, $N(R^8)_2$, $CF_3$, $NO_2$, $(R^8)O$—, $(R^9)S(O)_m$—, $(R^8)C(O)NH$—, $H_2N$—$C(NH)$—, $(R^8)C(O)$—, $(R^8)OC(O)$—, $N_3$, CN, $(R^9)OC(O)NR^8$—, $C_1-C_{20}$ alkyl, substituted or unsubstituted aryl and substituted or unsubstituted heterocycle;

$R^6$ is independently selected from:

a) hydrogen, b) $C_1-C_6$ alkyl, $C_2-C_6$ alkenyl, $C_2-C_6$ alkynyl, $C_1-C_6$ perfluoroalkyl, F, Cl, $R^8O$—, $R^8C(O)NR^8$—, CN, $NO_2$, $(R^8)_2N$—$C(NR^8)$—, $R^8C(O)$—, $R^8OC(O)$—, —$N(R^8)_2$, or $R^9OC(O)NR^8$—, and c) $C_1-C_6$ alkyl substituted by $C_1-C_6$ perfluoroalkyl, $R^8O$—, $R^8C(O)NR^8$—, $(R^8)_2N$—$C(NR^8)$—, $R^8C(O)$—, $R^8OC(O)$—, —$N(R^8)_2$, or $R^9OC(O)NR^8$—;

$R^7$ is selected from: hydrogen and $C_1-C_6$ alkyl;

$R^8$ is independently selected from hydrogen, $C_1-C_6$ alkyl, benzyl and aryl;

$R^9$ is independently selected from $C_1-C_6$ alkyl and aryl;

$R^{10}$ and $R^{11}$ are independently selected from: H;

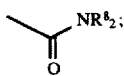

or $C_{1-5}$ alkyl, unbranched or branched, unsubstituted or substituted with one or more of:

1) aryl, 2) heterocycle,

3) $OR^8$,

4) $SR^9$, $SO_2R^9$, or

5)

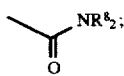

$A^1$ and $A^2$ are independently selected from: a bond, —CH=CH—, —C≡C—, —C(O)—, —C(O)NR^8—, O, —N(R^8)—, or $S(O)_m$;

V is selected from:

a) hydrogen, b) heterocycle selected from pyrrolidinyl, imidazolyl, pyridinyl, thiazolyl, pyridonyl, 2-oxopiperidinyl, indolyl, quinolinyl, isoquinolinyl, and thienyl, c) aryl, d) $C_1-C_{20}$ alkyl wherein from 0 to 4 carbon atoms are replaced with a heteroatom selected from O, S, and N, and e) $C_2-C_{20}$ alkenyl, and provided that V is not hydrogen if $A^1$ is $S(O)_m$ and V is not hydrogen if $A^1$ is a bond, n is 0 and $A^2$ is $S(O)_m$;

W is a heterocycle selected from pyrrolidinyl, pyridinyl, thiazolyl, pyridonyl, 2-oxopiperidinyl, indolyl, quinolinyl, or isoquinolinyl;

provided that when W is imidazolyl, then the substituent $(R^6)_r$—V—$A^1(CR^{1a}_2)_nA^2(CR^{1a}_2)_n$— is not H, $C_1-C_6$ alkyl or a nitrogen protecting group:

| | |
|---|---|
| m is | 0, 1 or 2; |
| n is | 0, 1, 2, 3 or 4; |
| p is | 0, 1, 2, 3 or 4; |
| q is | 0, 1, 2, 3 or 4; |
| r is | 0 to 5, provided that r is 0 when V is hydrogen; and |
| t is | 1; | or an optical isomer or pharmaceutically acceptable salt thereof.

4. The compound according to claim 1 of the formula Ic:

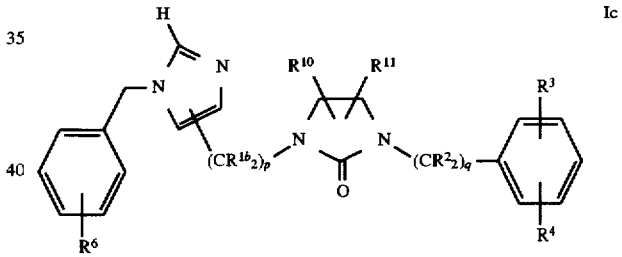

wherein:

$R^{1b}$ is independently selected from:

a) hydrogen, b) aryl, heterocycle, cycloalkyl, $R^8O$—, —$N(R^8)_2$ or $C_2-C_6$ alkenyl, c) $C_1-C_6$ alkyl unsubstituted or substituted by aryl, heterocycle, cycloalkyl, alkenyl, $R^8O$—, or —$N(R^8)_2$;

$R^2$ are independently selected from: hydrogen or $C_1-C_6$ alkyl;

$R^3$ and $R^4$ are independently selected from F, Cl, Br, $N(R^8)_2$, $CF_3$, $NO_2$, $(R^8)O$—, $(R^9)S(O)_m$—, $(R^8)C(O)NH$—, $H_2N$—$C(NH)$—, $(R^8)C(O)$—, $(R^8)OC(O)$—, $N_3$, CN, $(R^9)OC(O)NR^8$—, $C_1-C_{20}$ alkyl, substituted or unsubstituted aryl and substituted or unsubstituted heterocycle;

$R^6$ is independently selected from:

a) hydrogen, b) $C_1-C_6$ alkyl, $C_2-C_6$ alkenyl, $C_2-C_6$ alkynyl, $C_1-C_6$ perfluoroalkyl, F, Cl, $R^8O$—, $R^8C(O)NR^8$—, CN, $NO_2$, $(R^8)_2N$—$C(NR^8)$—, $R^8C(O)$—, $R^8OC(O)$—, —$N(R^8)_2$, or $R^9OC(O)NR^8$—, and c) $C_1-C_6$ alkyl substituted by $C_1-C_6$ perfluoroalkyl, $R^8O$—, $R^8C(O)NR^8$—, $(R^8)_2N$—$C(NR^8)$—, $R^8C(O)$—, $R^8OC(O)$—, —$N(R^8)_2$, or $R^9OC(O)NR^8$—;

R⁸ is independently selected from hydrogen, $C_1$-$C_6$ alkyl, benzyl and aryl;

R⁹ is independently selected from $C_1$-$C_6$ alkyl and aryl;

R¹⁰ and R¹¹ are independently selected from: H;

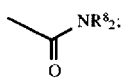

or $C_{1-5}$ alkyl, unbranched or branched, unsubstituted or substituted with one or more of:

1) aryl,
2) heterocycle,
3) OR⁸,
4) SR⁹, SO₂R⁹, or
5)

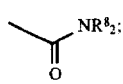

m is 0, 1 or 2;
p is 0, 1, 2, 3 or 4; and
q is 0, 1, 2, 3 or 4;

or an optical isomer or pharmaceutically acceptable salt thereof.

5. The compound according to claim 4 of the formula Id:

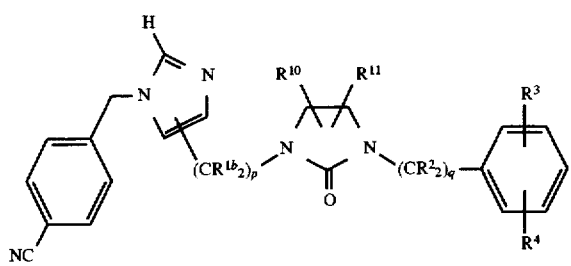

wherein:

R¹ᵇ is independently selected from:

a) hydrogen,
b) aryl, heterocycle, cycloalkyl, R⁸O—, —N(R⁸)₂ or $C_2$-$C_6$ alkenyl,
c) $C_1$-$C_6$ alkyl unsubstituted or substituted by aryl, heterocycle, cycloalkyl, alkenyl, R⁸O—, or —N(R⁸)₂;

R² are independently selected from: hydrogen or $C_1$-$C_6$ alkyl;

R³ and R⁴ are independently selected from F, Cl, Br, N(R⁸)₂, CF₃, NO₂, (R⁸)O—, (R⁹)S(O)ₘ—, (R⁸)C(O)NH—, H₂N—C(NH)—, (R⁸)C(O)—, (R⁸)OC(O)—, N₃, CN, (R⁹)OC(O)NR⁸—, $C_1$-$C_{20}$ alkyl, substituted or unsubstituted aryl and substituted or unsubstituted heterocycle;

R⁸ is independently selected from hydrogen, $C_1$-$C_6$ alkyl, benzyl and aryl;

R⁹ is independently selected from $C_1$-$C_6$ alkyl and aryl;

R¹⁰ and R¹¹ are independently selected from: H;

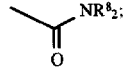

or $C_{1-5}$ alkyl, unbranched or branched, unsubstituted or substituted with one or more of:

1) aryl,
2) heterocycle,
3) OR⁸,
4) SR⁹, SO₂R⁹, or
5)

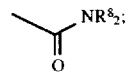

m is 0, 1 or 2;
p is 0, 1, 2, 3 or 4; and
q is 0, 1, 2, 3 or 4;

or an optical isomer or pharmaceutically acceptable salt thereof.

6. A compound which inhibits farnesyl-protein transferase which is:

(±)-4-(2-Butynyl)-1-(3-chlorophenyl)-3-[1-(4-cyanobenzyl)-5-imidazolylmethyl]-2-imidazolidinone (S)-4-n-butyl-3-[1-(4-cyanobenzyl)-5-imidazolylmethyl]-1-(2,3-dimethylphenyl)-2-imidazolidinone 1-(3-Chlorophenyl)-3-[1-(4-cyanobenzyl)-5-imidazolylmethyl]-2-imidazolidinone 4-(S)-4-n-Butyl-3-[4-chloro-1-(4-cyanobenzyl)-5-imidazolylmethyl]-1-(2-chloro-5,6-dimethylphenyl)-2-imidazolidinone (S)-1-(3-Chlorobenzyl)-3-[1-(4-cyanobenzyl)-5-imidazolylmethyl]-4-[(2-methanesulfonyl)ethyl]-2-imidazolidinone or a pharmaceutically acceptable salt or optical isomer thereof.

7. A compound which inhibits farnesyl-protein transferase which is:

(S)-1-(3-Chlorobenzyl)-3-[1-(4-cyanobenzyl)-5-imidazolylmethyl]-4-[(2-methanesulfonyl)ethyl]-2-imidazolidinone

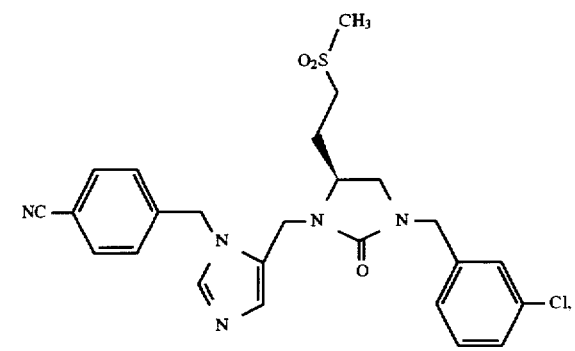

or a pharmaceutically acceptable salt or optical isomer thereof.

8. A pharmaceutical composition comprising a pharmaceutical carrier, and dispersed therein, a therapeutically effective amount of a compound of claim 1.

9. A pharmaceutical composition comprising a pharmaceutical carrier, and dispersed therein, a therapeutically effective amount of a compound of claim 2.

10. A pharmaceutical composition comprising a pharmaceutical carrier, and dispersed therein, a therapeutically effective amount of a compound of claim 3.

11. A pharmaceutical composition comprising a pharmaceutical carrier, and dispersed therein, a therapeutically effective amount of a compound of claim 6.

12. A method for inhibiting farnesyl-protein transferase which comprises administering to a mammal in need thereof a therapeutically effective amount of a composition of claim 8.

13. A method for inhibiting farnesyl-protein transferase which comprises administering to a mammal in need thereof a therapeutically effective amount of a composition of claim 9.

14. A method for inhibiting farnesyl-protein transferase which comprises administering to a mammal in need thereof a therapeutically effective amount of a composition of claim 10.

15. A method for inhibiting farnesyl-protein transferase which comprises administering to a mammal in need thereof a therapeutically effective amount of a composition of claim 11.

16. A method for inhibiting farnesyl-protein transferase which comprises administering to a mammal in need thereof a therapeutically effective amount of a composition comprising a pharmaceutical carrier, and dispersed therein, a therapeutically effective amount of a compound of formula I:

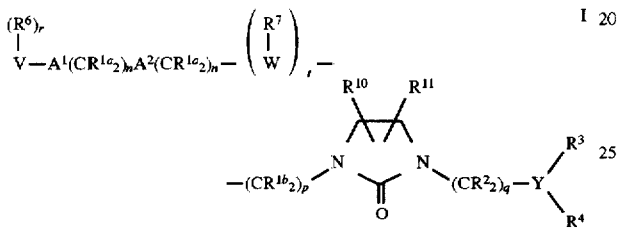

wherein:
$R^{1a}$, $R^{1b}$ and $R^2$ are independently selected from:
a) hydrogen,
b) aryl, heterocycle, $C_3$–$C_{10}$ cycloalkyl, $C_2$–$C_6$ alkenyl, $C_2$–$C_6$ alkynyl, $R^8O$—, $R^9S(O)_m$—, $R^8C(O)NR^8$—, CN, $NO_2$, $(R^8)_2N$—$C(NR^8)$—, $R^8C(O)$—, $R^8OC(O)$—, $N_3$, —$N(R^8)_2$, or $R^9OC(O)NR^8$—,
c) $C_1$–$C_6$ alkyl unsubstituted or substituted by aryl, heterocyclic, $C_3$–$C_{10}$ cycloalkyl, $C_2$–$C_6$ alkenyl, $C_2$–$C_6$ alkynyl, $R^8O$—, $R^9S(O)_m$—, $R^8C(O)NR^8$—, CN, $(R^8)_2N$—$C(NR^8)$—, $R^8C(O)$—, $R^8OC(O)$—, $N_3$, —$N(R^8)_2$, or $R^9OC(O)$—$NR^8$—;

$R^3$ and $R^4$ are independently selected from F, Cl, Br, $N(R^8)_2$, $CF_3$, $NO_2$, $(R^8)O$—, $(R^9)S(O)_m$—, $(R^8)C(O)NH$—, $H_2N$—$C(NH)$—, $(R^8)C(O)$—, $(R^8)OC(O)$—, $N_3$, CN, $CF_3(CH_2)_nO$—, $(R^9)OC(O)NR^8$—, $C_1$–$C_{20}$ alkyl, substituted or unsubstituted aryl and substituted or unsubstituted heterocycle;

$R^6$ is independently selected from:
a) hydrogen,
b) aryl, heterocycle, $C_3$–$C_{10}$ cycloalkyl, $C_2$–$C_6$ alkenyl, $C_2$–$C_6$ alkynyl, perfluoroalkyl, F, Cl, Br, $R^8O$—, $R^9S(O)_m$—, $R^8C(O)NR^8$—, CN, $NO_2$, $R^8_2N$—$C(NR^8)$—, $R^8C(O)$—, $R^8OC(O)$—, $N_3$, —$N(R^8)_2$, or $R^9OC(O)NR^8$—, and
c) $C_1$–$C_6$ alkyl unsubstituted or substituted by aryl, heterocycle, $C_3$–$C_{10}$ cycloalkyl, $C_2$–$C_6$ alkenyl, $C_2$–$C_6$ alkynyl, perfluoroalkyl, F, Cl, Br, $R^8O$—, $R^9S(O)_m$—, $R^8C(O)NH$—, CN, $H_2N$—$C(NH)$—, $R^8C(O)$—, $R^8OC(O)$—, $N_3$, —$N(R^8)_2$, or $R^8OC(O)NH$—;

$R^7$ is attached to a substitutable carbon on W and is selected from:
a) hydrogen,
b) $C_2$–$C_6$ alkenyl, $C_2$–$C_6$ alkynyl, perfluoroalkyl, F, Cl, Br, $R^8O$—, $R^9S(O)_m$—, $R^8C(O)NR^8$—, CN, $NO_2$, $(R^8)_2N$—$C$—$(NR^8)$—, $R^8C(O)$—, $R^8OC(O)$—, $N_3$, —$N(R^8)_2$, or $R^9OC(O)NR^8$—, and c) $C_1$–$C_6$ alkyl unsubstituted or substituted by perfluoroalkyl, F, Cl, Br, $R^8O$—, $R^9S(O)_m$—, $R^8C(O)NR^8$—, CN, $(R^8)_2N$—$C(NR^8)$—, $R^8C(O)$—, $R^8OC(O)$—, $N_3$, —$N(R^8)_2$, or $R^9OC(O)NR^8$—;

$R^8$ is independently selected from hydrogen, $C_1$–$C_6$ alkyl, benzyl and aryl;

$R^9$ is independently selected from $C_1$–$C_6$ alkyl and aryl;

$R^{10}$ and $R^{11}$ are independently selected from: H;

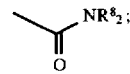

or $C_{1-5}$ alkyl, unbranched or branched, unsubstituted or substituted with one or more of:
1) aryl,
2) heterocycle,
3) $OR^8$,
4) $SR^9$, $SO_2R^9$, or
5)

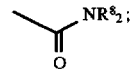

$A^1$ and $A^2$ are independently selected from: a bond, —CH=CH—, —C≡C—, —C(O)—, —C(O)NR^8—, —NR^8C(O)—, O, —N(R^8)—, —S(O)_2N(R^8)—, —N(R^8)S(O)_2—, or $S(O)_m$;

V is selected from:
a) hydrogen,
b) heterocycle,
c) aryl,
d) $C_1$–$C_{20}$ alkyl wherein from 0 to 4 carbon atoms are replaced with a a heteroatom selected from O, S, and N,
e) $C_2$–$C_{20}$ alkenyl, provided that V is not hydrogen if $A^1$ is $S(O)_m$ and V is not hydrogen if $A^1$ is a bond, n is 0 and $A^2$ is $S(O)_m$;

W is imidazolyl;
Y is aryl or heteroaryl;

| | |
|---|---|
| m is | 0, 1 or 2; |
| n is | 0, 1, 2, 3 or 4; |
| p is | 0, 1, 2, 3 or 4; |
| q is | 0, 1, 2, 3 or 4; |
| r is | 0 to 5, provided that r is 0 when V is hydrogen; and |
| t is | 1; | provided that the substitutent $(R^6)_r$—V—$A^1(CR^{1a}_2)_nA^2$ $(CR^{1a}_2)_n$— is independently selected from H, $C_1$–$C_6$ alkyl or a nitrogen protecting group;

or a pharmaceutically acceptable salt thereof.

17. A method for treating cancer which comprises administering to a mammal in need thereof a therapeutically effective amount of a composition of claim 8.

18. A method for treating cancer which comprises administering to a mammal in need thereof a therapeutically effective amount of a composition of claim 9.

19. A method for treating cancer which comprises administering to a mammal in need thereof a therapeutically effective amount of a composition of claim 10.

20. A method for treating cancer which comprises administering to a mammal in need thereof a therapeutically effective amount of a composition of claim 11.

21. A method for treating cancer which comprises administering to a mammal in need thereof a therapeutically effective amount of a composition comprising a pharmaceutical carrier, and dispersed therein, a therapeutically effective amount of a compound of formula I:

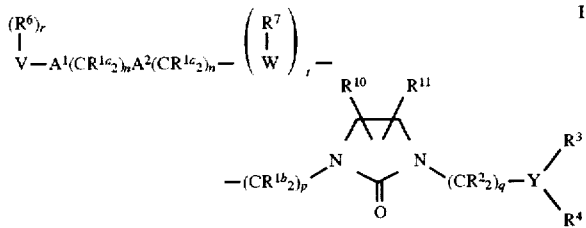

wherein:

$R^{1a}$, $R^{1b}$ and $R^2$ are independently selected from:

a) hydrogen, b) aryl, heterocycle, $C_3$–$C_{10}$ cycloalkyl, $C_2$–$C_6$ alkenyl, $C_2$–$C_6$ alkynyl, $R^8O$—, $R^9S(O)_m$—, $R^8C(O)NR^8$—, CN, $NO_2$, $(R^8)_2N$—$C(NR^8)$—, $R^8C(O)$—, $R^8OC(O)$—, $N_3$, —$N(R^8)_2$, or $R^9OC(O)NR^8$—, c) $C_1$–$C_6$ alkyl unsubstituted or substituted by aryl, heterocyclic, $C_3$–$C_{10}$ cycloalkyl, $C_2$–$C_6$ alkenyl, $C_2$–$C_6$ alkynyl, $R^8O$—, $R^9S(O)_m$—, $R^8C(O)NR^8$—, CN, $(R^8)_2N$—$C(NR^8)$—, $R^8C(O)$—, $R^8OC(O)$—, $N_3$, —$N(R^8)_2$, or $R^9OC(O)$—$NR^8$—;

$R^3$ and $R^4$ are independently selected from F, Cl, Br, $N(R^8)_2$, $CF_3$, $NO_2$, $(R^8)O$—, $(R^9)S(O)$—, $(R^8)C(O)NH$—, $H_2N$—$C(NH)$—, $(R^8)C(O)$—, $(R^8)OC(O)$—, $N_3$, CN, $CF_3(CH_2)_nO$—, $(R^9)OC(O)NR^8$—, $C_1$–$C_{20}$ alkyl, substituted or unsubstituted aryl and substituted or unsubstituted heterocycle;

$R^6$ is independently selected from:

a) hydrogen, b) aryl, heterocycle, $C_3$–$C_{10}$ cycloalkyl, $C_2$–$C_6$ alkenyl, $C_2$–$C_6$ alkynyl, perfluoroalkyl, F, Cl, Br, $R^8O$—, $R^9S(O)_m$—, $R^8C(O)NR^8$—, CN, $NO_2$, $R^8_2N$—$C(NR^8)$—, $R^8C(O)$—, $R^8OC(O)$—, $N_3$, —$N(R^8)_2$, or $R^9OC(O)NR^8$—, and c) $C_1$–$C_6$ alkyl unsubstituted or substituted by aryl, heterocycle, $C_3$–$C_{10}$ cycloalkyl, $C_2$–$C_6$ alkenyl, $C_2$–$C_6$ alkynyl, perfluoroalkyl, F, Cl, Br, $R^8O$—, $R^9S(O)_m$—, $R^8C(O)NH$—, CN, $H_2N$—$C(NH)$—, $R^8C(O)$—, $R^8OC(O)$—, $N_3$, —$N(R^8)_2$, or $R^8OC(O)NH$—;

$R^7$ is attached to a substitutable carbon on W and is selected from:

a) hydrogen, b) $C_2$–$C_6$ alkenyl, $C_2$–$C_6$ alkynyl, perfluoroalkyl, F, Cl, Br, $R^8O$—, $R^9S(O)_m$—, $R^8C(O)NR^8$—, CN, $NO_2$, $(R^8)_2N$—$C$—$(NR^8)$—, $R^8C(O)$—, $R^8OC(O)$—, $N_3$, —$N(R^8)_2$, or $R^9OC(O)NR^8$—, and c) $C_1$–$C_6$ alkyl unsubstituted or substituted by perfluoroalkyl, F, Cl, Br, $R^8O$—, $R^9S(O)_m$—, $R^8C(O)NR^8$—, CN, $(R^8)_2N$—$C(NR^8)$—, $R^8C(O)$—, $R^8OC(O)$—, $N_3$, —$N(R^8)_2$, or $R^9OC(O)NR^8$—;

$R^8$ is independently selected from hydrogen, $C_1$–$C_6$ alkyl, benzyl and aryl;

$R^9$ is independently selected from $C_1$–$C_6$ alkyl and aryl;

$R^{10}$ and $R^{11}$ are independently selected from: H;

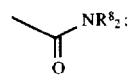

or $C_{1-5}$ alkyl, unbranched or branched, unsubstituted or substituted with one or more of:

1) aryl, 2) heterocycle,

3) $OR^8$,

4) $SR^9$, $SO_2R^9$, or

5)

$$\overset{NR^8_2}{\underset{O}{\|}}$$

$A^1$ and $A^2$ are independently selected from: a bond, —CH=CH—, —C≡C—, —C(O)—, —C(O)NR^8—, —NR^8C(O)—, O, —N(R^8)—, —S(O)_2N(R^8)—, —N(R^8)S(O)_2—, or $S(O)_m$;

V is selected from:

a) hydrogen, b) heterocycle, c) aryl, d) $C_1$–$C_{20}$ alkyl wherein from 0 to 4 carbon atoms are replaced with a a heteroatom selected from O, S, and N, and e) $C_2$–$C_{20}$ alkenyl, provided that V is not hydrogen if $A^1$ is $S(O)_m$ and V is not hydrogen if $A^1$ is a bond, n is 0 and $A^2$ is $S(O)_m$;

W is imidazolyl;

Y is aryl or heteroaryl;

| | |
|---|---|
| m is | 0, 1 or 2; |
| n is | 0, 1, 2, 3 or 4; |
| p is | 0, 1, 2, 3 or 4; |
| q is | 0, 1, 2, 3 or 4; |
| r is | 0 to 5, provided that r is 0 when V is hydrogen; and |
| t is | 1; | provided that the substitutent $(R^6)_r$—V—$A^1(CR^{1a}_2)_nA^2(CR^{1a}_2)_n$— is independently selected from H, $C_1$–$C_6$ alkyl or a nitrogen protecting group;

or a pharmaceutically acceptable salt thereof.

22. A method for treating neurofibromen benign proliferative disorder which comprises administering to a mammal in need thereof a therapeutically effective amount of a composition of claim 8.

23. A method for treating blindness related to retinal vascularization which comprises administering to a mammal in need thereof a therapeutically effective amount of a composition of claim 8.

24. A method for treating infections from hepatitis delta and related viruses which comprises administering to a mammal in need thereof a therapeutically effective amount of a composition of claim 8.

25. A method for preventing restenosis which comprises administering to a mammal in need thereof a therapeutically effective amount of a composition of claim 8.

26. A method for treating polycystic kidney disease which comprises administering to a mammal in need thereof a therapeutically effective amount of a composition of claim 8.

* * * * *

UNITED STATES PATENT AND TRADEMARK OFFICE
CERTIFICATE OF CORRECTION

PATENT NO. : 5,780,492

DATED : July 14, 1998

INVENTOR(S) : Christopher J. Dinsmore and Theresa M. Williams

It is certified that error appears in the above-identified patent and that said Letters Patent is hereby corrected as shown below:

The structures in Claims 1, 16 and 21 should be shown on one line.

Claim 1 - Column 39 between lines 45 and 55

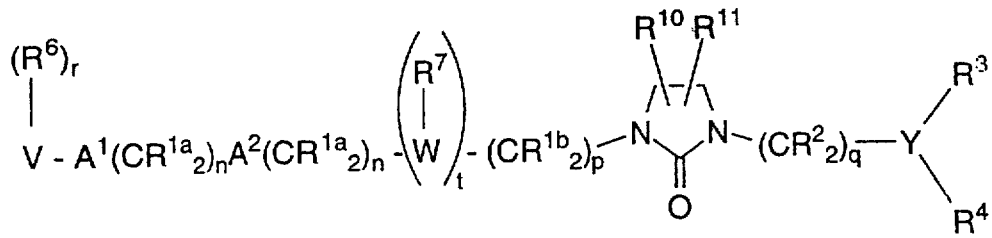

Claim 16 - Column 47 between lines 20 and 30

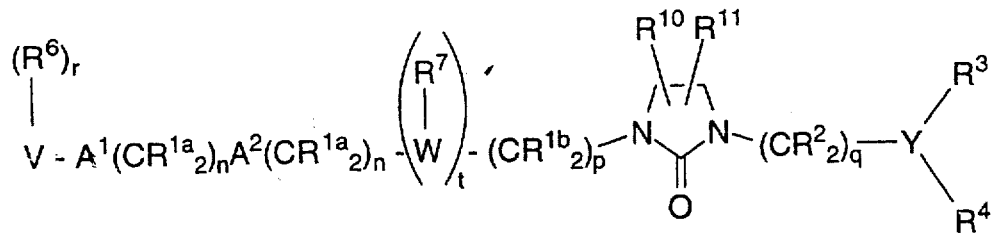

UNITED STATES PATENT AND TRADEMARK OFFICE
CERTIFICATE OF CORRECTION

PATENT NO. : 5,780,492

DATED : July 14, 1998

INVENTOR(S) : Christopher J. Dinsmore and Theresa J. Williams

It is certified that error appears in the above-identified patent and that said Letters Patent is hereby corrected as shown below:

Claim 21 - Column 49 between lines 7 and 15

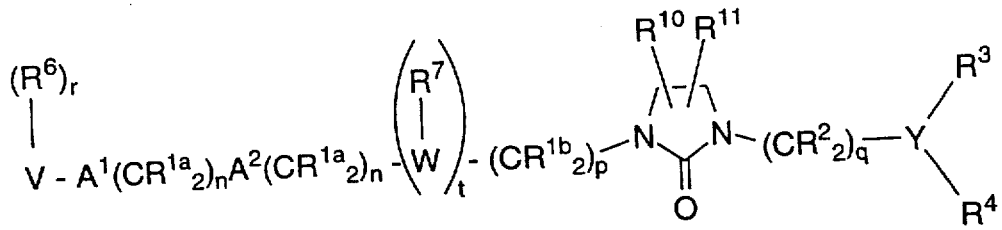

Signed and Sealed this

Tenth Day of November 1998

Attest:

BRUCE LEHMAN

Attesting Officer

Commissioner of Patents and Trademarks